(12) United States Patent
Purcell

(10) Patent No.: US 11,603,413 B2
(45) Date of Patent: Mar. 14, 2023

(54) ANTI-TMPRSS2 ANTIBODIES AND ANTIGEN-BINDING FRAGMENTS

(71) Applicant: REGENERON PHARMACEUTICALS, INC., Tarrytown, NY (US)

(72) Inventor: Lisa Purcell, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 221 days.

(21) Appl. No.: 17/153,684

(22) Filed: Jan. 20, 2021

(65) Prior Publication Data

US 2021/0230303 A1 Jul. 29, 2021
US 2022/0081489 A9 Mar. 17, 2022

Related U.S. Application Data

(62) Division of application No. 16/256,560, filed on Jan. 24, 2019, now Pat. No. 10,941,213.

(60) Provisional application No. 62/622,292, filed on Jan. 26, 2018.

(51) Int. Cl.
| | | |
|---|---|---|
| *C07K 14/435* | (2006.01) | |
| *C07K 16/00* | (2006.01) | |
| *A61K 39/395* | (2006.01) | |
| *A61K 39/00* | (2006.01) | |
| *A61K 39/42* | (2006.01) | |
| *C07K 16/40* | (2006.01) | |
| *A61P 31/16* | (2006.01) | |
| *A61K 9/00* | (2006.01) | |
| *C07K 16/10* | (2006.01) | |
| *C07K 16/28* | (2006.01) | |
| *C12N 9/64* | (2006.01) | |

(52) U.S. Cl.
CPC ............ *C07K 16/40* (2013.01); *A61K 9/0019* (2013.01); *A61P 31/16* (2018.01); *C07K 16/1018* (2013.01); *C07K 16/28* (2013.01); *C07K 16/283* (2013.01); *C12N 9/6424* (2013.01); *A61K 2039/505* (2013.01); *A61K 2039/507* (2013.01); *A61K 2039/54* (2013.01); *C07K 2317/21* (2013.01); *C07K 2317/24* (2013.01); *C07K 2317/31* (2013.01); *C07K 2317/52* (2013.01); *C07K 2317/565* (2013.01); *C07K 2317/76* (2013.01); *C07K 2317/92* (2013.01); *C07K 2317/94* (2013.01); *C07K 2319/30* (2013.01)

(58) Field of Classification Search
CPC ............ C07K 2317/76; C07K 16/1018; A61K 2039/505; A61K 39/42
See application file for complete search history.

(56) References Cited

U.S. PATENT DOCUMENTS

| 9,498,529 B2 | 11/2016 | Purcell Ngambo |
| 2013/0273070 A1 | 10/2013 | Purcell Ngambo |

FOREIGN PATENT DOCUMENTS

| CA | 2672622 C | 5/2016 |
| WO | WO2002/004953 | 1/2002 |
| WO | WO2008/076379 | 6/2008 |
| WO | WO2008/127347 | 10/2008 |
| WO | WO2013/158516 | 10/2013 |
| WO | WO2017/151453 | 9/2017 |
| WO | WO2018/175749 | 9/2018 |

OTHER PUBLICATIONS

Bertram et al. (2010) "TMPRSS2 and TMPRSS4 Facilitate Trypsin-Independent Spread of Influenza Virus in Caco-2 Cells", Journal of Virology, 84, 10016-10025.
Bonkhoff (2018) "Estrogen Receptor Signaling in Prostate Cancer: Implications for Carcinogenesis and Tumor Progression", Prostate, 78(1): 2-10.
Bottcher et al. (2006) "Proteolytic Activation of Influenza Viruses by Serine Proteases TMPRSS2 and HAT from Human Airway Epithelium", Journal of Virology, 80(19):9896-8.
Bottcher-Friebertsauser et al. (2011) "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology, 85, 1554-1562.
Database UniParc [Online] UniParc; (Mar. 12, 2003).
De Nardis Camilla et al. (2017) "Recombinant Expression of the Full-length Ecto domain of LDL Receptor-related Protein 1 (LRP1) Unravels pH dependent Conformational Changes and the Stoichiometry of Binding with Receptor-associated Protein (RAP)", The Journal of Biological Chemistry, vol. 292, No. 3.
Reinke et al. (2017) "Different Residues in the SARS-CoV Spike Protein Determine Cleavage and Activation by the Host Cell Protease TMPRSS2", PLoS ONE, 12,e0179177.
Shen et al. (2017) "TMPRSS2: A Potential Target for Treatment of Influenza Virus and Coronavirus Infections", Biochimie, 142: 1-10.
Shirato et al. (2017) "Clinical Isolates of Human Coronavirus 229E Bypass the Endosome for Cell Entry", Journal of Virology, 91, e01387-16.
Tarnow et al. (2014) "TMPRSS2 is a Host Factor That is Essential for Pneumotropism and Pathogenicity of H7N9 Influenza A Virus in Mice", Journal of Virology, 88(9):4744-51.
Wilson et al. (2005) "The Membrane-Anchored Serine Protease, TMPRSS2, Activates PAR-2 in Prostate Cancer Cells", The Biochemical Journal, vol. 388, No. Pt. 3.

(Continued)

*Primary Examiner* — Barry A Chestnut
(74) *Attorney, Agent, or Firm* — FisherBroyles, LLP; Cara L. Crowley-Weber; Gabriele Amodeo

(57) ABSTRACT

The present invention includes an antibody or antigen-binding fragment thereof that binds specifically to TMPRSS2 and methods of using such antibodies and fragments for treating or preventing viral infections (e.g., influenza virus infections).

20 Claims, 9 Drawing Sheets

Specification includes a Sequence Listing.

(56) References Cited

OTHER PUBLICATIONS

Zhou et al. (2015) "Protease Inhibitors Targeting Coronavirus and Filo Virus Entry", Antiviral Research, 116, 76-84.

Zmora et al. (2015) "TMPRSS2 Isoform 1 Activates Respiratory Viruses and IsExpressed in Viral Target Cells", PLoS ONE, 10, e0138380.

Zmora et al. (2017) "Non-human Primate Orthologues of TMPRSS2 Cleave and Activate the Influenza Virus Hemagglutinin", PLoS ONE, 12, e0176597.

International Search Report and Written Opinion for International Application No. PCTUS2019/014978 dated May 10, 2019, 21 pages.

```
                              SEQUENCE LISTING

<160> NUMBER OF SEQ ID NOS: 48

<210> SEQ ID NO 1
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 1 cag gtg cag ctg gtg gag tct ggg gga ggc gtg gtc cag cct ggg agg       48
Gln Val Gln Leu Val Glu Ser Gly Gly Gly Val Val Gln Pro Gly Arg
1               5                   10                  15 tcc ctg aga ctc tcc tgt gca gcg tct gga ttc acc ttc agt tcc tat       96
Ser Leu Arg Leu Ser Cys Ala Ala Ser Gly Phe Thr Phe Ser Ser Tyr
            20                  25                  30 ggc atg cac tgg gtc cgc cag tct cca ggc aag ggg ctc gag tgg gtg      144
Gly Met His Trp Val Arg Gln Ser Pro Gly Lys Gly Leu Glu Trp Val
        35                  40                  45 gca gtt ata tgg aat gat gga agt tat gta tac tat gca gac tcc gtg      192
Ala Val Ile Trp Asn Asp Gly Ser Tyr Val Tyr Tyr Ala Asp Ser Val
    50                  55                  60 aag ggc cga ttc acc atc tcc aga gac att tcc aag aac acg ctg ttt      240
Lys Gly Arg Phe Thr Ile Ser Arg Asp Ile Ser Lys Asn Thr Leu Phe
65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95 gcg aga gag ggg gag tgg gta ctt tac tac ttt gac tac tgg ggc cag      336
Ala Arg Glu Gly Glu Trp Val Leu Tyr Tyr Phe Asp Tyr Trp Gly Gln
            100                 105                 110 gga acc ctg gtc acc gtc tcc tca                                      360
Gly Thr Leu Val Thr Val Ser Ser
        115                 120

<210> SEQ ID NO 2
<211> LENGTH: 120
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ser Pro Gly Lys Gly Leu Glu Trp Val
        35                  40                  45
```

```
Ala Val Ile Trp Asn Asp Gly Ser Tyr Val Tyr Tyr Ala Asp Ser Val
 50                  55                  60

Lys Gly Arg Phe Thr Ile Ser Arg Asp Ile Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Glu Gly Glu Trp Val Leu Tyr Tyr Phe Asp Tyr Trp Gly Gln
            100                 105                 110

Gly Thr Leu Val Thr Val Ser Ser
        115                 120

<210> SEQ ID NO 3
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 3 gac atc cag atg acc cag tct cct tcc acc ctg tct gca tct gtt gga      48
Asp Ile Gln Met Thr Gln Ser Pro Ser Thr Leu Ser Ala Ser Val Gly
 1               5                  10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
             20                  25                  30 ttg gcc tgg tat cag cag aaa cca ggg aaa gcc cct aaa ctc ctg atc     144
Leu Ala Trp Tyr Gln Gln Lys Pro Gly Lys Ala Pro Lys Leu Leu Ile
         35                  40                  45 tat aag gcg tct act tta gaa agt ggg gtc cca tca agg ttc agc ggc     192
Tyr Lys Ala Ser Thr Leu Glu Ser Gly Val Pro Ser Arg Phe Ser Gly
 50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
 65                  70                  75                  80 gat gat ttt gca act tat tac tgc caa cag tat aat agt tat tcg tac     288
Asp Asp Phe Ala Thr Tyr Tyr Cys Gln Gln Tyr Asn Ser Tyr Ser Tyr
                 85                  90                  95 act ttt ggc cag ggg acc aag ctg gag atc aaa                         321
Thr Phe Gly Gln Gly Thr Lys Leu Glu Ile Lys
            100                 105

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Thr Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80
```

```
Asp Asp Phe Ala Thr Tyr Tyr Cys Gln Gln Tyr Asn Ser Tyr Ser Tyr
                85                  90                  95
Thr Phe Gly Gln Gly Thr Lys Leu Glu Ile Lys
        100                 105

<210> SEQ ID NO 5
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 5 gga ttc acc ttc agt tcc tat ggc                                         24
Gly Phe Thr Phe Ser Ser Tyr Gly
1               5

<210> SEQ ID NO 6
<211> LENGTH: 8
<212> TYPE: PRT
<213> ORGANISM: Homo sapiens

<400> SEQUENCE: 6

Gly Phe Thr Phe Ser Ser Tyr Gly
1               5

<210> SEQ ID NO 7
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 7 ata tgg aat gat gga agt tat gta                                         24
Ile Trp Asn Asp Gly Ser Tyr Val
1               5

<210> SEQ ID NO 8
<211> LENGTH: 8
<212> TYPE: PRT
<213> ORGANISM: Homo sapiens

<400> SEQUENCE: 8

Ile Trp Asn Asp Gly Ser Tyr Val
1               5

<210> SEQ ID NO 9
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 9 gcg aga gag ggg gag tgg gta ctt tac tac ttt gac tac                     39
Ala Arg Glu Gly Glu Trp Val Leu Tyr Tyr Phe Asp Tyr
1               5                   10

<210> SEQ ID NO 10
<211> LENGTH: 13
<212> TYPE: PRT
<213> ORGANISM: Homo sapiens
```

<400> SEQUENCE: 10

Ala Arg Glu Gly Glu Trp Val Leu Tyr Tyr Phe Asp Tyr
1               5                   10

<210> SEQ ID NO 11
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 11 cag agt att agt agc tgg                                            18
Gln Ser Ile Ser Ser Trp
1               5

<210> SEQ ID NO 12
<211> LENGTH: 6
<212> TYPE: PRT
<213> ORGANISM: Homo sapiens

<400> SEQUENCE: 12

Gln Ser Ile Ser Ser Trp
1               5

<210> SEQ ID NO 13
<211> LENGTH: 9
<212> TYPE: DNA
<213> ORGANISM: Homo sapiens

<400> SEQUENCE: 13 aaggcgtct                                                           9

<210> SEQ ID NO 14
<211> LENGTH: 3
<212> TYPE: PRT
<213> ORGANISM: Homo sapiens

<400> SEQUENCE: 14

Lys Ala Ser
1

<210> SEQ ID NO 15
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 15 caa cag tat aat agt tat tcg tac act                                27
Gln Gln Tyr Asn Ser Tyr Ser Tyr Thr
1               5

<210> SEQ ID NO 16
<211> LENGTH: 9
<212> TYPE: PRT
<213> ORGANISM: Homo sapiens

<400> SEQUENCE: 16

Gln Gln Tyr Asn Ser Tyr Ser Tyr Thr
1               5

<210> SEQ ID NO 17
<211> LENGTH: 450
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ser Pro Gly Lys Gly Leu Glu Trp Val
        35                  40                  45

Ala Val Ile Trp Asn Asp Gly Ser Tyr Val Tyr Tyr Ala Asp Ser Val
    50                  55                  60

Lys Gly Arg Phe Thr Ile Ser Arg Asp Ile Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Gly Glu Trp Val Leu Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 214
<212> TYPE: PRT
<213> ORGANISM: Homo sapiens

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 447
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ser Pro Gly Lys Gly Leu Glu Trp Val
        35                  40                  45
Ala Val Ile Trp Asn Asp Gly Ser Tyr Val Tyr Tyr Ala Asp Ser Val
50                  55                  60
Lys Gly Arg Phe Thr Ile Ser Arg Asp Ile Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Arg Glu Gly Glu Trp Val Leu Tyr Tyr Phe Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445
```

```
<210> SEQ ID NO 20
<211> LENGTH: 178
<212> TYPE: PRT
<213> ORGANISM: Homo sapiens

<400> SEQUENCE: 20

Trp Lys Phe Met Gly Ser Lys Cys Ser Asn Ser Gly Ile Glu Cys Asp
1               5                   10                  15

Ser Ser Gly Thr Cys Ile Asn Pro Ser Asn Trp Cys Asp Gly Val Ser
            20                  25                  30

His Cys Pro Gly Gly Glu Asp Glu Asn Arg Cys Val Arg Leu Tyr Gly
        35                  40                  45

Pro Asn Phe Ile Leu Gln Met Tyr Ser Ser Gln Arg Lys Ser Trp His
    50                  55                  60

Pro Val Cys Gln Asp Asp Trp Asn Glu Asn Tyr Gly Arg Ala Ala Cys
65                  70                  75                  80

Arg Asp Met Gly Tyr Lys Asn Asn Phe Tyr Ser Ser Gln Gly Ile Val
                85                  90                  95

Asp Asp Ser Gly Ser Thr Ser Phe Met Lys Leu Asn Thr Ser Ala Gly
            100                 105                 110

Asn Val Asp Ile Tyr Lys Lys Leu Tyr His Ser Asp Ala Cys Ser Ser
        115                 120                 125

Lys Ala Val Val Ser Leu Arg Cys Ile Ala Cys Gly Val Asn Leu Asn
    130                 135                 140

Ser Ser Arg Gln Ser Arg Glu Gln Lys Leu Ile Ser Glu Glu Asp Leu
145                 150                 155                 160

Gly Gly Glu Gln Lys Leu Ile Ser Glu Glu Asp Leu His His His His
                165                 170                 175

His His

<210> SEQ ID NO 21
<211> LENGTH: 178
<212> TYPE: PRT
<213> ORGANISM: Macaca fascicularis

<400> SEQUENCE: 21

Trp Lys Phe Met Gly Ser Lys Cys Ser Asp Ser Gly Ile Glu Cys Asp
1               5                   10                  15

Ser Ser Gly Thr Cys Ile Ser Leu Ser Asn Trp Cys Asp Gly Val Ser
            20                  25                  30

His Cys Pro Asn Gly Glu Asp Glu Asn Arg Cys Val Arg Leu Tyr Gly
        35                  40                  45

Pro Asn Phe Ile Leu Gln Val Tyr Ser Ser Gln Arg Lys Ser Trp His
    50                  55                  60

Pro Val Cys Arg Asp Asp Trp Asn Glu Asn Tyr Ala Arg Ala Ala Cys
65                  70                  75                  80

Arg Asp Met Gly Tyr Lys Asn Ser Phe Tyr Ser Ser Gln Gly Ile Val
                85                  90                  95

Asp Asn Ser Gly Ala Thr Ser Phe Met Lys Leu Asn Thr Ser Ala Gly
            100                 105                 110

Asn Val Asp Ile Tyr Lys Lys Leu Tyr His Ser Asp Ala Cys Ser Ser
        115                 120                 125

Lys Ala Val Val Ser Leu Arg Cys Ile Ala Cys Gly Val Arg Ser Asn
    130                 135                 140

Leu Ser Arg Gln Ser Arg Glu Gln Lys Leu Ile Ser Glu Glu Asp Leu
145                 150                 155                 160
```

Gly Gly Glu Gln Lys Leu Ile Ser Glu Glu Asp Leu His His His
                165                 170                 175

His His

<210> SEQ ID NO 22
<211> LENGTH: 492
<212> TYPE: PRT
<213> ORGANISM: Homo sapiens

<400> SEQUENCE: 22

Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
                20                  25                  30

Val Pro Thr Val Tyr Glu Val His Pro Ala Gln Tyr Tyr Pro Ser Pro
            35                  40                  45

Val Pro Gln Tyr Ala Pro Arg Val Leu Thr Gln Ala Ser Asn Pro Val
        50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
                100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
        130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
                180                 185                 190

Asn Phe Tyr Ser Ser Gln Gly Ile Val Asp Asp Ser Gly Ser Thr Ser
            195                 200                 205

Phe Met Lys Leu Asn Thr Ser Ala Gly Asn Val Asp Ile Tyr Lys Lys
        210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
                260                 265                 270

Leu His Val Gln Asn Val His Val Cys Gly Gly Ser Ile Ile Thr Pro
            275                 280                 285

Glu Trp Ile Val Thr Ala Ala His Cys Val Glu Lys Pro Leu Asn Asn
        290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
                340                 345                 350

```
Lys Pro Leu Thr Phe Asn Asp Leu Val Lys Pro Val Cys Leu Pro Asn
            355                 360                 365

Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
            435                 440                 445

Lys Asn Asn Ile Trp Trp Leu Ile Gly Asp Thr Ser Trp Gly Ser Gly
450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490

<210> SEQ ID NO 23
<211> LENGTH: 492
<212> TYPE: PRT
<213> ORGANISM: Macaca mulatta

<400> SEQUENCE: 23

Met Ala Leu Asn Ser Gly Ser Pro Pro Gly Val Gly Pro Tyr Tyr Glu
1               5                   10                  15

Asn His Gly Tyr Gln Pro Glu Asn Pro Tyr Pro Ala Gln Pro Thr Val
                20                  25                  30

Ala Pro Asn Val Tyr Glu Val His Pro Ala Gln Tyr Tyr Pro Ser Pro
            35                  40                  45

Val Pro Gln Tyr Thr Pro Arg Val Leu Thr His Ala Ser Asn Pro Ala
50                  55                  60

Val Cys Arg Gln Pro Lys Ser Pro Ser Gly Thr Val Cys Thr Ser Lys
65                  70                  75                  80

Thr Lys Lys Ala Leu Cys Val Thr Met Thr Leu Gly Ala Val Leu Val
                85                  90                  95

Gly Ala Ala Leu Ala Ala Gly Leu Leu Trp Lys Phe Met Gly Ser Lys
            100                 105                 110

Cys Ser Asp Ser Gly Ile Glu Cys Asp Ser Ser Gly Thr Cys Ile Ser
        115                 120                 125

Leu Ser Asn Trp Cys Asp Gly Val Ser His Cys Pro Asn Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Arg Asp Asp Trp
                165                 170                 175

Asn Glu Asn Tyr Ala Arg Ala Ala Cys Arg Asp Met Gly Tyr Lys Asn
            180                 185                 190

Ser Phe Tyr Ser Ser Gln Gly Ile Val Asp Asn Ser Gly Ala Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240
```

```
Cys Ile Ala Cys Gly Val Arg Ser Asn Leu Ser Arg Gln Ser Arg Ile
                245                 250                 255

Val Gly Gly Gln Asn Ala Leu Leu Gly Ala Trp Pro Trp Gln Val Ser
            260                 265                 270

Leu His Val Gln Asn Ile His Val Cys Gly Gly Ser Ile Ile Thr Pro
        275                 280                 285

Glu Trp Ile Val Thr Ala Ala His Cys Val Glu Lys Pro Leu Asn Ser
    290                 295                 300

Pro Trp Gln Trp Thr Ala Phe Val Gly Thr Leu Arg Gln Ser Ser Met
305                 310                 315                 320

Phe Tyr Glu Lys Gly His Arg Val Glu Lys Val Ile Ser His Pro Asn
                325                 330                 335

Tyr Asp Ser Lys Thr Lys Asn Asn Asp Ile Ala Leu Met Lys Leu His
            340                 345                 350

Thr Pro Leu Thr Phe Asn Glu Val Val Lys Pro Val Cys Leu Pro Asn
        355                 360                 365

Pro Gly Met Met Leu Glu Pro Glu Gln His Cys Trp Ile Ser Gly Trp
    370                 375                 380

Gly Ala Thr Gln Glu Lys Gly Lys Thr Ser Asp Val Leu Asn Ala Ala
385                 390                 395                 400

Met Val Pro Leu Ile Glu Pro Arg Arg Cys Asn Asn Lys Tyr Val Tyr
                405                 410                 415

Asp Gly Leu Ile Thr Pro Ala Met Ile Cys Ala Gly Phe Leu Gln Gly
            420                 425                 430

Thr Val Asp Ser Cys Gln Gly Asp Ser Gly Gly Pro Leu Val Thr Leu
        435                 440                 445

Lys Asn Asp Val Trp Trp Leu Ile Gly Asp Thr Ser Trp Gly Ser Gly
    450                 455                 460

Cys Ala Gln Ala Asn Arg Pro Gly Val Tyr Gly Asn Val Thr Val Phe
465                 470                 475                 480

Thr Asp Trp Ile Tyr Arg Gln Met Arg Ala Asp Gly
                485                 490

<210> SEQ ID NO 24
<211> LENGTH: 120
<212> TYPE: PRT
<213> ORGANISM: Homo sapiens

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Phe
            20                  25                  30

Ser Met Asn Trp Val Arg Gln Val Pro Gly Lys Gly Leu Glu Trp Val
        35                  40                  45

Ser Ser Ile Ser Thr Ser Gly Asn Tyr Met Tyr Tyr Ala Asp Ser Val
    50                  55                  60

Lys Gly Arg Phe Thr Ile Ser Arg Asp Asn Ala Lys Lys Ser Phe Ser
65                  70                  75                  80

Leu Gln Met Asn Ser Leu Arg Ala Glu Asp Ser Ala Ile Tyr Tyr Cys
                85                  90                  95

Ala Arg Gly Gly Gly Tyr Asn Trp Asn Leu Phe Asp Tyr Trp Gly Gln
            100                 105                 110

Gly Ser Leu Val Thr Val Ser Ser
        115                 120
```

```
<210> SEQ ID NO 25
<211> LENGTH: 8
<212> TYPE: PRT
<213> ORGANISM: Homo sapiens

<400> SEQUENCE: 25

Gly Phe Thr Phe Ser Gly Phe Ser
1               5

<210> SEQ ID NO 26
<211> LENGTH: 8
<212> TYPE: PRT
<213> ORGANISM: Homo sapiens

<400> SEQUENCE: 26

Ile Ser Thr Ser Gly Asn Tyr Met
1               5

<210> SEQ ID NO 27
<211> LENGTH: 13
<212> TYPE: PRT
<213> ORGANISM: Homo sapiens

<400> SEQUENCE: 27

Ala Arg Gly Gly Gly Tyr Asn Trp Asn Leu Phe Asp Tyr
1               5                   10

<210> SEQ ID NO 28
<211> LENGTH: 108
<212> TYPE: PRT
<213> ORGANISM: Homo sapiens

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Ser Glu Asp Phe Ala Val Tyr Tyr Cys Gln Gln Tyr Gly Asn Ser Pro
                85                  90                  95

Leu Thr Phe Gly Gly Gly Thr Lys Val Glu Ile Lys
            100                 105

<210> SEQ ID NO 29
<211> LENGTH: 7
<212> TYPE: PRT
<213> ORGANISM: Homo sapiens

<400> SEQUENCE: 29

Gln Ser Leu Asn Ser Asn Tyr
1               5

<210> SEQ ID NO 30
<211> LENGTH: 3
<212> TYPE: PRT
<213> ORGANISM: Homo sapiens
```

```
<400> SEQUENCE: 30

Gly Ala Ser
1

<210> SEQ ID NO 31
<211> LENGTH: 9
<212> TYPE: PRT
<213> ORGANISM: Homo sapiens

<400> SEQUENCE: 31

Gln Gln Tyr Gly Asn Ser Pro Leu Thr
1               5

<210> SEQ ID NO 32
<211> LENGTH: 120
<212> TYPE: PRT
<213> ORGANISM: Homo sapiens

<400> SEQUENCE: 32

Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Pro Tyr Ala Gln Lys Phe
    50                  55                  60

Gln Asp Arg Val Thr Ile Thr Thr Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Gln Pro Val Tyr Gln Tyr Asn Met Asp Val Trp Gly Gln
            100                 105                 110

Gly Thr Thr Val Thr Val Ser Ser
        115                 120

<210> SEQ ID NO 33
<211> LENGTH: 8
<212> TYPE: PRT
<213> ORGANISM: Homo sapiens

<400> SEQUENCE: 33

Gly Gly Thr Phe Ser Ser Tyr Ala
1               5

<210> SEQ ID NO 34
<211> LENGTH: 8
<212> TYPE: PRT
<213> ORGANISM: Homo sapiens

<400> SEQUENCE: 34

Ile Ile Pro Ile Phe Gly Thr Pro
1               5

<210> SEQ ID NO 35
<211> LENGTH: 13
<212> TYPE: PRT
<213> ORGANISM: Homo sapiens
```

<400> SEQUENCE: 35

Ala Arg Gln Gln Pro Val Tyr Gln Tyr Asn Met Asp Val
1               5                   10

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Gln Lys Pro Leu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Asn Tyr Pro Trp
                85                  90                  95

Thr Phe Gly Gln Gly Thr Lys Val Glu Ile Lys
            100                 105

<210> SEQ ID NO 37
<211> LENGTH: 6
<212> TYPE: PRT
<213> ORGANISM: Homo sapiens

<400> SEQUENCE: 37

Gln Gly Ile Arg Asn Asn
1               5

<210> SEQ ID NO 38
<211> LENGTH: 3
<212> TYPE: PRT
<213> ORGANISM: Homo sapiens

<400> SEQUENCE: 38

Ala Ala Ser
1

<210> SEQ ID NO 39
<211> LENGTH: 9
<212> TYPE: PRT
<213> ORGANISM: Homo sapiens

<400> SEQUENCE: 39

Leu Gln Tyr Asn Asn Tyr Pro Trp Thr
1               5

<210> SEQ ID NO 40
<211> LENGTH: 120
<212> TYPE: PRT
<213> ORGANISM: Homo sapiens

<400> SEQUENCE: 40

Glu Val Gln Leu Val Glu Ser Gly Gly Leu Val Lys Pro Gly Gly
1               5                   10                  15

Ser Leu Arg Leu Ser Cys Ala Ala Ser Gly Phe Ser Phe Ser Gly Phe
            20                  25                  30

Ser Met Asn Trp Val Arg Gln Ala Pro Gly Lys Gly Leu Glu Trp Val
        35                  40                  45

Ser Ser Ile Ser Thr Ser Gly Asn Tyr Met Tyr Tyr Ala Asp Ser Val
    50                  55                  60

Lys Gly Arg Phe Thr Ile Ser Arg Asp Asn Ala Lys Lys Ser Phe Ser
65                  70                  75                  80

Leu Gln Met Asn Ser Leu Arg Ala Glu Asp Ser Ala Ile Tyr Tyr Cys
                85                  90                  95

Ala Arg Gly Gly Gly Tyr Asn Trp Asn Leu Phe Asp Tyr Trp Gly Gln
            100                 105                 110

Gly Ser Leu Val Thr Val Ser Ser
        115                 120

<210> SEQ ID NO 41
<211> LENGTH: 8
<212> TYPE: PRT
<213> ORGANISM: Homo sapiens

<400> SEQUENCE: 41

Gly Phe Ser Phe Ser Gly Phe Ser
1               5

<210> SEQ ID NO 42
<211> LENGTH: 8
<212> TYPE: PRT
<213> ORGANISM: Homo sapiens

<400> SEQUENCE: 42

Ile Ser Thr Ser Gly Asn Tyr Met
1               5

<210> SEQ ID NO 43
<211> LENGTH: 13
<212> TYPE: PRT
<213> ORGANISM: Homo sapiens

<400> SEQUENCE: 43

Ala Arg Gly Gly Gly Tyr Asn Trp Asn Leu Phe Asp Tyr
1               5                   10

<210> SEQ ID NO 44
<211> LENGTH: 108
<212> TYPE: PRT
<213> ORGANISM: Homo sapiens

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Ala Asp Phe Thr Leu Thr Ile Ser Arg Leu Glu
 65                  70                  75                  80

Ser Glu Asp Phe Ala Val Tyr Tyr Cys Gln Gln Tyr Gly Asn Ser Pro
                 85                  90                  95

Leu Thr Phe Gly Gly Gly Thr Lys Val Glu Ile Lys
            100                 105

<210> SEQ ID NO 45
<211> LENGTH: 7
<212> TYPE: PRT
<213> ORGANISM: Homo sapiens

<400> SEQUENCE: 45

Gln Ser Leu Asn Ser Asn Tyr
 1               5

<210> SEQ ID NO 46
<211> LENGTH: 3
<212> TYPE: PRT
<213> ORGANISM: Homo sapiens

<400> SEQUENCE: 46

Gly Ala Ser
 1

<210> SEQ ID NO 47
<211> LENGTH: 9
<212> TYPE: PRT
<213> ORGANISM: Homo sapiens

<400> SEQUENCE: 47

Gln Gln Tyr Gly Asn Ser Pro Leu Thr
 1               5

<210> SEQ ID NO 48
<211> LENGTH: 5
<212> TYPE: PRT
<213> ORGANISM: Artificial Sequence
<220> FEATURE:
<223> OTHER INFORMATION: GS Linker

<400> SEQUENCE: 48

Gly Gly Gly Gly Ser
 1               5
```

ANTI-TMPRSS2 ANTIBODIES AND ANTIGEN-BINDING FRAGMENTS

This application is a Divisional Application of U.S. patent application Ser. No. 16/256,560, filed Jan. 24, 2019, which claims the benefit under 35 U.S.C. § 119(e) of U.S. Provisional Application No. 62/622,292, filed Jan. 26, 2018; the disclosure of which is herein incorporated by reference in its entirety.

FIELD OF THE INVENTION

The present invention relates to antibodies and antigen-binding fragments that bind specifically to TMPRSS2 and methods for treating or preventing viral infections with said antibodies and fragments.

BACKGROUND OF THE INVENTION

Influenza viruses have acquired resistance to currently used drugs that target the viral neuraminidase (NA) or the ion channel protein, matrix protein 2 (M2). The emergence of drug resistance highlights the need for the development of novel antiviral strategies. Host cell targeting may reduce or avoid the emergence of escape mutants, but could create a "sink" due to widespread expression and raise the concern for toxicity. A number of respiratory virus fusion proteins have been shown to require cleavage by host protease(s) for activation (Shirato et al. Clinical Isolates of Human Coronavirus 229E Bypass the Endosome for Cell Entry. Journal of Virology. 91, e01387-16 (2017); Reinke et al., Different residues in the SARS-CoV spike protein determine cleavage and activation by the host cell protease TMPRSS2. PLoS ONE. 12, e0179177 (2017); Zhou et al., Protease inhibitors targeting coronavirus and filovirus entry. Antiviral Research. 116, 76-84 (2015); Zmora et al. TMPRSS2 Isoform 1 Activates Respiratory Viruses and Is Expressed in Viral Target Cells. PLoS ONE. 10, e0138380 (2015)), including influenza (Zmora et al., Non-human primate orthologues of TMPRSS2 cleave and activate the influenza virus hemagglutinin. PLoS ONE. 12, e0176597 (2017); Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011); Bertram et al., TMPRSS2 and TMPRSS4 facilitate trypsin-independent spread of influenza virus in Caco-2 cells. Journal of Virology. 84, 10016-10025 (2010); Tarnow et al., TMPRSS2 is a host factor that is essential for pneumotropism and pathogenicity of H7N9 influenza A virus in mice. Journal of Virology (2014), May; 88(9):4744-51).

Influenza A hemagglutinin precursor (HA0) requires cleavage by a host serine protease, to HA1 and HA2, for activation. For example, transmembrane protease, serine 2; TMPRSS2, TMPRSS4 and TMPRSS11D as well as human airway trypsin-like protease (HAT) have been implicated in HA cleavage (Bertram et al., TMPRSS2 and TMPRSS4 facilitate trypsin-independent spread of influenza virus in Caco-2 cells. Journal of Virology. 84, 10016-10025 (2010); Bottcher et al., Proteolytic Activation of Influenza Viruses by Serine Proteases TMPRSS2 and HAT from Human Airway Epithelium. Journal of Virology. 2006 October; 80(19):9896-8; International patent application publication no. WO2017/151453). Also, TMPRSS2 is a target for anti-cancer therapy. See e.g., WO2008127347 and WO2002004953. A fusion between TMPRSS2 and ERG (TMPRSS2:ERG) is a gene fusion known to be a major driver of prostate carcinogenesis which is triggered by the ERα and repressed by the ERβ. Bonkhoff, Estrogen receptor signaling in prostate cancer: Implications for carcinogenesis and tumor progression, Prostate 78(1): 2-10 (2018).

SUMMARY OF THE INVENTION

Although there are small molecule inhibitors of TMPRSS2 and research antibodies, useful, for example, for immunohistochemistry, there is a need in the art for neutralizing therapeutic anti-TMPRSS2 antibodies and their use for treating or preventing viral infection. See e.g., Shen et al. Biochimie 142: 1-10 (2017), WO2008127347; WO2002004953; U.S. Pat. No. 9,498,529; antibody ab92323, available from Abcam (Cambridge, Mass.) or antibodies sc-515727 and sc-101847 available from Santa Cruz Biotech (Dallas, Tex.). The present invention addresses this need, in part, by providing human anti-human TMPRSS2 antibodies, such as H1H7017N, and combinations thereof including, for example, anti-influenza HA antibodies (e.g., Group I HA or Group II HA) and methods of use thereof for treating viral infections.

The present invention provides a neutralizing human antigen-binding protein that specifically binds to human TMPRSS2, for example, an antibody or antigen-binding fragment thereof. For example, in an embodiment of the invention, the antigen-binding protein comprises: (a) the CDR-H1, CDR-H2, and CDR-H3 of an immunoglobulin heavy chain that comprises the amino acid sequence set forth in SEQ ID NO: 2, 17 or 19; and/or (b) the CDR-L1, CDR-L2, and CDR-L3 of an immunoglobulin light chain that comprises the amino acid sequence set forth in SEQ ID NO: 4 or 18. In an embodiment of the invention, the antigen-binding protein comprises: (a) a light chain immunoglobulin variable region comprising an amino acid sequence having at least 90% amino acid sequence identity to the amino acid sequence set forth in SEQ ID NO: 4 or 18; and/or (b) a heavy chain immunoglobulin variable region comprising an amino acid sequence having at least 90% amino acid sequence identity to the amino acid sequence set forth in SEQ ID NO: 2, 17 or 19. In an embodiment of the invention, the present invention provides antigen-binding protein comprising: (a) CDR-L1, CDR-L2 and CDR-L3 of a light chain immunoglobulin comprising an amino acid sequence set forth in SEQ ID NO: 4 or 18 and at least 90% amino acid sequence identity to the amino acid sequence set forth in SEQ ID NO: 4 or 18; and/or (b) CDR-H1, CDR-H2 and CDR-H3 of a heavy chain immunoglobulin comprising an amino acid sequence set forth in SEQ ID NO: 2, 17 or 19 and at least 90% amino acid sequence identity to the amino acid sequence set forth in SEQ ID NO: 2, 17 or 19. For example, in an embodiment of the invention, the antigen-binding protein comprises a light chain immunoglobulin variable region that comprises (a) a CDR-H1 comprising the amino acid sequence: G F T F S S Y G (SEQ ID NO: 6); (b) a CDR-H2 comprising the amino acid sequence: I W N D G S Y V (SEQ ID NO: 8); (c) a CDR-H3 comprising the amino acid sequence: A R E G E W V L Y Y F D Y (SEQ ID NO: 10); and a heavy chain immunoglobulin variable region that comprises (a) a CDR-L1 comprising the amino acid sequence: Q S I S S W (SEQ ID NO: 12); (b) a CDR-L2 comprising the amino acid sequence: K A S (SEQ ID NO: 14); and/or (c) a CDR-L3 comprising the amino acid sequence: Q Q Y N S Y S Y T (SEQ ID NO: 16). The present invention also provides an antigen-binding protein comprising: (a) a heavy chain immunoglobulin that comprises the amino acid sequence set forth in SEQ ID NO: 17 or 19; and/or (b) a light chain immunoglobulin that comprises the amino acid sequence set forth in SEQ ID NO: 18.

The present invention also provides any anti-TMPRSS2 antigen-binding protein that competes with any antigen-binding protein that is set forth herein for binding to TMPRSS2 (e.g., as determined by use of using a real time, label-free bio-layer interferometry assay, e.g., on an Octet RED384 biosensor (Pall ForteBio Corp.)); or which binds to the same or an overlapping epitope on TMPRSS2 (or a fragment thereof) as any antigen-binding protein that is set forth herein.

The present invention also provides multispecific antigen-binding proteins that bind to TMPRSS2 and another antigen or to TMPRSS2 at a different epitope. For example, the multispecific molecule comprises (a) a first antigen-binding domain that binds specifically to TMPRSS2; and (b) a second antigen-binding domain that binds specifically to another antigen or to TMPRSS2 or to an epitope which differs from that of the first antigen-binding domain.

The present invention also provides any anti-TMPRSS2 antigen-binding protein (e.g., an antibody or antigen-binding fragment, e.g., comprising a sequence set forth herein) that comprises one or more of the following properties:
Inhibits growth of influenza virus (e.g., A/Puerto Rico/ 08/1934 (H1N1)) in TMPRSS2-expressing cells (e.g., Calu-3 cells);
Binds to the surface of TMPRSS-expressing cells (e.g., MDCK/Tet-on), e.g., with an $EC_{50}$ value of 440 pM or 1.06 nM;
Does not significantly bind to MDCK/Tet-on cells which do not express TMPRSS2;
Binds to human TMPRSS2 with a $K_D$ of about $2.81 \times 10^{-9}$ M at about 25° C.;
Binds to human TMPRSS2 with a $K_D$ of about $9.31 \times 10^{-9}$ M at about 37° C.;
Binds to cynomolgus TMPRSS2 with a $K_D$ of about $5.60 \times 10^{-8}$ M at about 25° C.;
Binds to cynomolgus TMPRSS2 with a $K_D$ of about $1.40 \times 10^{-7}$ M at about 37° C.;
Limits spread of influenza virus infection of cells in vitro; and/or
Protects a mouse engineered to express the human TMPRSS2 protein from death caused by influenza virus infection.

The present invention also provides a complex comprising any antigen-binding protein set forth herein bound to a TMPRSS2 polypeptide, e.g., in vitro or in the body of a subject.

The present invention also provides a method for making an anti-TMPRSS2 antigen-binding protein set forth herein (e.g., H1H7017N) or immunoglobulin chain thereof comprising: (a) introducing one or more polynucleotides encoding a light and/or a heavy immunoglobulin chain of the said antigen-binding protein; (b) culturing the host cell (e.g., CHO cell, *Pichia* cell or *Pichia pastoris* cell) under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method is part of the present invention.

A polypeptide (e.g., an immunoglobulin) comprising: (a) CDR1, CDR2, and CDR3 of a VH domain of an immunoglobulin chain that comprises the amino acid sequence set forth in SEQ ID NO: 2; or (b) CDR1, CDR2, and CDR3 of a VL domain of an immunoglobulin chain that comprises the amino acid sequence set forth in SEQ ID NO: 4 (e.g., wherein the polypeptide is in a host cell) also forms part of the present invention.

The present invention also provides a polynucleotide (e.g., DNA or RNA) that encoded a polypeptide of the present invention. In an embodiment of the invention, the polynucleotide encodes two different immunoglobulin chains (e.g., heavy and light). In an embodiment of the invention, one polynucleotide encodes a light immunoglobulin chain and another polynucleotide encodes a heavy immunoglobulin chain, e.g., wherein the chains are in a host cell or are in a vessel. For example, the polynucleotide is in a vector (e.g., a plasmid) and/or is integrated into a host cell chromosome.

Host cells (e.g., CHO cell, *Pichia* cell or *Pichia pastoris* cell) of the present invention may include an anti-TMPRSS2 antigen-binding protein (e.g., H1H7017N), polypeptide thereof or polynucleotide encoding such a polypeptide and/or a vector including such a polynucleotide.

The present invention also provides a composition or kit comprising an anti-TMPRSS2 antigen-binding protein set forth herein (e.g., H1H7017N) in association with a further therapeutic agent (e.g., an anti-viral drug and/or a vaccine). For example, the composition may be a pharmaceutical composition comprising the antigen-binding protein and pharmaceutically acceptable carrier and, optionally, a further therapeutic agent. The further therapeutic agent may be ledipasvir, sofosbuvir, a combination of ledipasvir and sofosbuvir, oseltamivir, zanamivir, ribavirin and interferon-alpha2b, interferon-alpha2a and/or an antibody or antigen-binding fragment thereof that specifically binds to influenza HA. In an embodiment of the invention, the further therapeutic agent is an antibody or antigen binding fragment thereof selected from the group consisting of H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B;

H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B.

In an embodiment of the invention, a further therapeutic agent which is provided in association with an anti-TM-PRSS2 antigen-binding protein is an antibody or antigen-binding fragment that binds to influenza Group II HA protein, such as H1H14611N2; or an antibody or fragment that comprises VH and VL of H1H14611N2; or a heavy chain immunoglobulin comprising CDR-H1, CDR-H2 and CDR-H3 of H1H14611N2 (e.g., SEQ ID NOs: 25-27) and a light chain immunoglobulin comprising CDR-L1, CDR-L2 and CDR-L3 of H1H14611N2 (e.g., SEQ ID NOs: 29-31).

In an embodiment of the invention, a further therapeutic agent which is provided in association with an anti-TM-PRSS2 antigen-binding protein is an antibody or antigen-binding fragment that binds to influenza Group II HA protein, such as H1H14612N2; or an antibody or fragment that comprises VH and VL of H1H14612N2; or a heavy chain immunoglobulin comprising CDR-H1, CDR-H2 and CDR-H3 of H1H14612N2 (e.g., SEQ ID NOs: 41-43) and a light chain immunoglobulin comprising CDR-L1, CDR-L2 and CDR-L3 of H1H14612N2 (e.g., SEQ ID NOs: 45-47).

In an embodiment of the invention, a further therapeutic agent which is provided in association with an anti-TM-PRSS2 antigen-binding protein is an antibody or antigen-binding fragment that binds to influenza Group I HA protein, such as H1H11729P; or an antibody or fragment that comprises VH and VL of H1H11729P; or a heavy chain immunoglobulin comprising CDR-H1, CDR-H2 and CDR-H3 of H1H11729P (e.g., SEQ ID NOs: 33-35) and a light chain immunoglobulin comprising CDR-L1, CDR-L2 and CDR-L3 of H1H11729P (e.g., SEQ ID NOs: 37-39).

The present invention also provides a vessel or injection device that comprises an anti-TMPRSS2 antigen-binding protein (e.g., H1H7017N) or composition thereof (e.g., pharmaceutical composition).

The present invention also provides a method for treating or preventing a viral infection other than an influenza virus infection, in a subject (e.g., a human) in need thereof, comprising administering a therapeutically effective amount of anti-TMPRSS2 antigen-binding protein set forth herein (e.g., H1H7017N).

The present invention also provides a method for treating or preventing cancer (e.g., prostate cancer) or infection, e.g., a viral infection, e.g., an infection with an influenza virus, coronavirus, SARS-Co virus, MERS-Co virus, parainfluenza virus, human metapneumovirus or hepatitis C virus (HCV), in a subject (e.g., a human) in need thereof, comprising administering a therapeutically effective amount of anti-TMPRSS2 antigen-binding protein set forth herein (e.g., H1H7017N). For example, the antigen-binding protein is administered in association with one or more further therapeutic agents (e.g., anti-viral drug and/or a vaccine). In an embodiment of the invention, a further therapeutic agent is a member selected from the group consisting of: ledipasvir, sofosbuvir, a combination of ledipasvir and sofosbuvir, oseltamivir, zanamivir, ribavirin and interferon-alpha2b, interferon-alpha2a and an antibody or antigen-binding fragment thereof that specifically binds to influenza HA. In an embodiment of the invention, a further therapeutic agent is an antibody or antigen binding fragment thereof selected from the group consisting of H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2;

H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B.

The present invention also provides a method for administering an anti-TMRPSS2 antigen-binding protein (e.g., H1H7017N) set forth herein into the body of a subject (e.g., a human) comprising injecting the antigen-binding protein into the body of the subject parenterally (e.g., subcutaneously, intravenously or intramuscularly).

DETAILED DESCRIPTION OF THE INVENTION

Figure 1A:
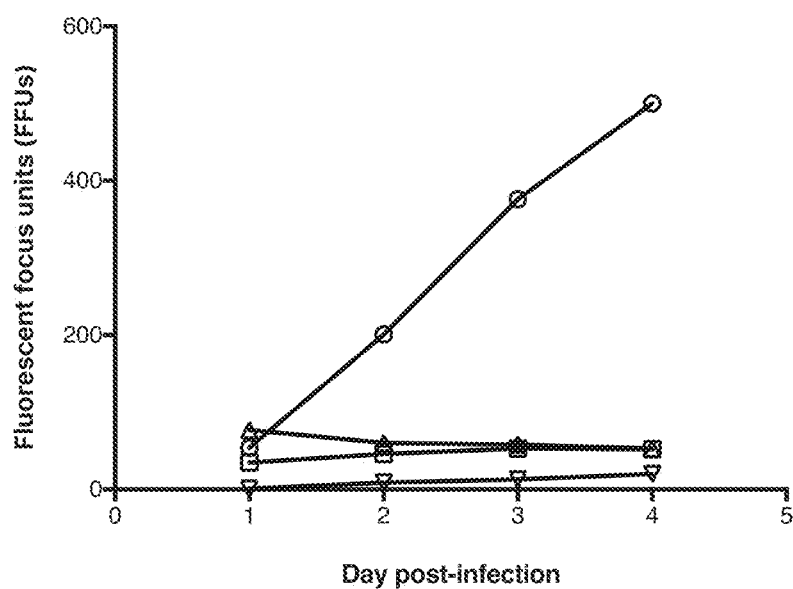
FIG. 1A shows the progression of the A/Puerto Rico/08/1934 (H1N1)-GFP virus spreading in different cell lines with an initial multiplicity of infection of 0.01 in absence of exogenous trypsin. Calu3 (circle), A549 (square), MDCK (triangle) and HepG2 (inverted triangle) cells.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "influenza hemagglutinin", also called "influenza HA" is a trimeric glycoprotein found on the surface of influenza virions, which mediates viral attachment (via HA1 binding to α-2,3- and α-2,6-sialic acids) and entry (through conformational change) into host cells. The HA is comprised of two structural domains: a globular head domain containing the receptor binding site (subject to high frequency of antigenic mutations) and the stem region (more conserved among various strains of influenza virus). The influenza HA is synthesized as a precursor (HA0) that undergoes proteolytic processing to produce two subunits (HA1 and HA2) which associate with one another to form the stem/globular head structure. The viral HA is the most variable antigen on the virus and the stem (HA2) is highly conserved within each group.

The term "influenza neuraminidase", also called "influenza NA" is an exosialidase (EC 3.2.1.18) which cleaves α-ketosidic linkage between the sialic (N-acetylneuraminic) acid and an adjacent sugar residue.

The amino acid sequence of full-length Influenza HA is exemplified by the amino acid sequence of influenza isolate H1N1 A/California/04/2009 provided in Gen Bank as accession number FJ966082.1. The term "influenza-HA" also includes protein variants of influenza HA isolated from different influenza isolates, e.g., GQ149237.1, NC_002017, KM972981.1, etc. The term "influenza-HA" also includes recombinant influenza HA or a fragment thereof. The term also encompasses influenza HA or a fragment thereof coupled to, for example, histidine tag, mouse or human Fc, or a signal sequence.

An anti-TMPRSS2 "antigen-binding protein" is a polypeptide or complex of more than one polypeptide (e.g., a tetrameric IgG antibody) that binds specifically to TMPRSS2 polypeptide, for example, an anti-TMPRSS2 antibody or antigen-binding fragment whether monospecific or multispecific.

TMPRSS2

TMPRSS2 (Transmembrane protease serine 2) is a protein, located on human chromosome 21, that belongs to the serine protease family (type II transmembrane serine proteases (TTSPs)) which is important for influenza virus infectivity. TMPRSS2 has been demonstrated to mediate cleavage of influenza virus HA0 to HA1 and HA2.

The human TMPRSS2 gene encodes a predicted protein of 492 amino acids which anchors to the plasma membrane. The protein converts to its mature form through autocatalytic cleavage between Arg255 and Ile256. After cleavage, the mature proteases are mostly membrane bound, yet a portion of them may be liberated into the extracellular milieu.

In an embodiment of the invention, human TMPRSS2 (V160M) comprises the amino acid sequence:

MALNSGSPPAIGPYYENHGYQPENPYPAQPTVVPTVYEVHPAQYYPSPVP

QYAPRVLTQASNPVVCTQPKSPSGTVCTSKTKKALCITLTLGTFLVGAAL

AAGLLWKFMGSKCSNSGIECDSSGTCINPSNWCDGVSHCPGGEDENRCVR

LYGPNFILQMYSSQRKSWHPVCQDDWNENYGRAACRDMGYKNNFYSSQGI

VDDSGSTSFMKLNTSAGNVDIYKKLYHSDACSSKAVVSLRCIACGVNLNS

SRQSRIVGGESALPGAWPWQVSLHVQNVHVCGGSIITPEWIVTAAHCVEK

PLNNPWHWTAFAGILRQSFMFYGAGYQVEKVISHPNYDSKTKNNDIALMK

LQKPLTFNDLVKPVCLPNPGMMLQPEQLCWISGWGATEEKGKTSEVLNAA

KVLLIETQRCNSRYVYDNLITPAMICAGFLQGNVDSCQGDSGGPLVTSKN

NIWWLIGDTSWGSGCAKAYRPGVYGNVMVFTDWIYRQMRADG (SEQ ID NO: 22; methionine 160 in bold font). In an embodiment of the invention, the TMPRSS2 polypeptide does not comprise the V160M mutation. See also NM_005656.3.

In an embodiment of the invention, *Macaca mulatta* TMPRSS2 (S129L, N251S, I415V, R431Q, D492G) comprises the amino acid sequence:

MALNSGSPPGVGPYYENHGYQPENPYPAQPTVAPNVYEVHPAQYYPSPVP

QYTPRVLTHASNPAVCRQPKSPSGTVCTSKTKKALCVTMTLGAVLVGAAL

AAGLLWKFMGSKCSDSGIECDSSGTCISLSNWCDGVSHCPNGEDENRCVR

LYGPNFILQVYSSQRKSWHPVCRDDWNENYARAACRDMGYKNSFYSSQGI

VDNSGATSFMKLNTSAGNVDIYKKLYHSDACSSKAVVSLRCIACGVRSNL

SRQSRIVGGQNALLGAWPWQVSLHVQNIHVCGGSIITPEWIVTAAHCVEK

PLNSPWQWTAFVGTLRQSSMFYEKGHRVEKVISHPNYDSKTKNNDIALMK

LHTPLTFNEVVKPVCLPNPGMMLEPEQHCWISGWGATQEKGKTSDVLNAA

MVPLIEPRRCNNKYVYDGLITPAMICAGFLQGTVDSCQGDSGGPLVTLKN

DVWWLIGDTSWGSGCAQANRPGVYGNVTVFTDWIYRQMRADG (SEQ ID NO: 23). In an embodiment of the invention, the TMPRSS2 polypeptide does not comprise the S129L, N251S, I415V, R431Q and/or D492G mutation.

In an embodiment of the invention, *Mus musculus* TMPRSS2 mRNA comprises the nucleotide sequence set forth in NM_015775.2.

Viruses

The present invention includes methods for treating or preventing a viral infection in a subject. The term "virus" includes any virus whose infection in the body of a subject is treatable or preventable by administration of an anti-TMPRSS2 antibody or antigen-binding fragment thereof (e.g., wherein infectivity of the virus is at least partially dependent on TMPRSS2). In an embodiment of the invention, a "virus" is any virus that expresses HA0 or another substrate of TMPRSS2 whose proteolytic cleavage is required for full infectivity of the virus against a cell in a host. The term "virus" also includes a TMPRSS2-dependent respiratory virus which is a virus that infects the respiratory tissue of a subject (e.g., upper and/or lower respiratory tract, trachea, bronchi, lungs) and is treatable or preventable by administration of an anti-TMPRSS2. For example, in an embodiment of the invention, virus includes influenza virus, coronavirus, SARS-Co virus (severe acute respiratory syndrome coronavirus), MERS-Co virus (middle east respiratory syndrome (MERS) CoV), parainfluenza virus, sendai virus (SeV), human metapneumovirus and/or hepatitis C virus (HCV). "Viral infection" refers to the invasion and multiplication of a virus in the body of a subject. The present invention includes embodiments with a proviso that "virus" excludes influenza virus, e.g., wherein viral infection excludes influenza virus infection.

There are now two genera of human parainfluenza virus (HPIV), respirovirus (HPIV-1 and HPIV-3) and rubulavirus (HPIV-2 and HPIV-4). Both genera (paramyxoviruses) can be separated morphologically from influenza virus.

Sendai virus, also known as murine parainfluenza virus, is the type species in the genus respirovirus, which also contains the species human parainfluenza virus 3, bovine parainfluenza virus 3, and human parainfluenza virus 1. TMPRSS2 Is an Activating Protease for Respiratory Parainfluenza Viruses such as parainfluenza viruses and Sendai virus (SeV). See et al. Abe et al., J. Virol. 87(21): 11930-11935 (2013).

Human metapneumovirus (HMPV) is classified as the first human member of the Metapneumovirus genus in the Pneumovirinae subfamily within the Paramyxoviridae family. It is an enveloped negative-sense single-stranded RNA virus. The RNA genome includes 8 genes coding for 9 different proteins. HMPV is identical in gene order to the avian pneumovirus (AMPV), which also belongs to the Metapneumovirus genus. TMPRSS2 is expressed in the human lung epithelium, cleaves the HMPV F protein efficiently and supports HMPV multiplication and may be involved in the development of lower respiratory tract illness in HMPV-infected patients. See et al. Shirogane et al. J Virol. 82(17): 8942-8946 (2008).

Hepatitis C virus (HCV) is a small, enveloped, positive-sense single-stranded RNA virus of the family Flaviviridae. HCV, with at least 6 genotypes and numerous subtypes, is a member of the hepacivirus genus. TMPRSS2 may activate HCV infection at the post-binding and entry stage. Esumi et al., Hepatology 61(2): 437-446 (2015).

Influenza viruses are members of the family Orthomyxoviridae. This family represents enveloped viruses the genome of which has segmented negative-sense single-strand RNA segments. There are four genera of this family: types A, B, C and Thogotovirus. The Influenza viruses classes, A, B and C, are based on core protein and are further divided into subtypes determined by the viral envelope glycoproteins hemagglutinin (HA) and neuraminidase (NA) (e.g., subtype A/H1N1). There are at least 18 influenza hemagglutinin ("HA") protein subtypes (H1-H18 or HA1-HA18) and at least 11 influenza neuraminidase (NA) protein subtypes (N1-N11 or NA1-NA11) used to define influenza subtypes. Group 1 influenza has H1, H2, H5, H6, H8, H9, H11, H12, H13, H16, H17 and H18 subtypes and NAB, NA5, Na4 and NA1 subtypes. Group 2 has H3, H4, H7, H10, H14 and H15 subtypes and NA6, NA9, NA7, NA2 and NA3 subtypes. Influenza A viruses infect a range of mammalian and avian species, whereas type B and C infections are largely restricted to humans. The eight genome segments of influenza A and B viruses are loosely encapsidated by the nucleoprotein.

Coronavirus virions are spherical with diameters of approximately 125 nm. The most prominent feature of coronaviruses is the club-shape spike projections emanating from the surface of the virion. These spikes are a defining feature of the virion and give them the appearance of a solar corona, prompting the name, coronaviruses. Within the envelope of the virion is the nucleocapsid. Coronaviruses have helically symmetrical nucleocapsids, which is uncommon among positive-sense RNA viruses, but far more common for negative-sense RNA viruses. Both MERS-CoV (middle east respiratory syndrome coronavirus) and SARS-CoV (severe acute respiratory syndrome coronavirus) belong to the coronavirus family. The initial attachment of the virion to the host cell is initiated by interactions between the S protein and its receptor. The sites of receptor binding domains (RBD) within the S1 region of a coronavirus S protein vary depending on the virus, with some having the RBD at the C-terminus of S1. The S-protein/receptor interaction is the primary determinant for a coronavirus to infect a host species and also governs the tissue tropism of the virus. Many coronaviruses utilize peptidases as their cellular receptor. Following receptor binding, the virus must next gain access to the host cell cytosol. This is generally accomplished by acid-dependent proteolytic cleavage of S protein by a cathepsin, TMPRRS2 or another protease, followed by fusion of the viral and cellular membranes.

Anti-TMPRSS2 Antibodies and Antigen-Binding Fragments

The present invention provides antigen-binding proteins, such as antibodies and antigen-binding fragments thereof, that specifically bind to TMPRSS2 protein or an antigenic fragment thereof.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof (e.g. IgM)—for example, H1H7017N. Each heavy chain comprises a heavy chain variable region ("HCVR" or "VH") (e.g., SEQ ID NO 2) and a heavy chain constant region (comprised of domains CH1, CH2 and CH3). Each light chain is comprised of a light chain variable region ("LCVR or "VL") (e.g., SEQ ID NO 4) and a light chain constant region (CL). The VH and VL regions can be further subdivided into regions of hypervariability, termed complementarity determining regions (CDR), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences, or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

The present invention includes monoclonal anti-TMPRSS2 antigen-binding proteins, e.g., antibodies and antigen-binding fragments thereof, as well as monoclonal compositions comprising a plurality of isolated monoclonal antigen-binding proteins. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-TMPRSS2 antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment comprises a light chain constant domain, e.g., of the type kappa or lambda.

The term "human" antigen-binding protein, such as an antibody, as used herein, includes antibodies having variable and constant regions derived from human germline immunoglobulin sequences whether in a human cell or grafted into a non-human cell, e.g., a mouse cell. See e.g., U.S. Pat. No. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject. See below.

The present invention includes anti-TMPRSS2 chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (U.S. Pat. No. 4,816, 567; and Morrison et al., (1984) Proc. Natl. Acad. Sci. USA 81: 6851-6855).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) expression system or isolated from a recombinant combinatorial human antibody library.

Recombinant anti-TMPRSS2 antigen-binding proteins, e.g., antibodies and antigen-binding fragments, disclosed herein may also be produced in an E. coli/T7 expression system. In this embodiment, nucleic acids encoding the anti-TMPRSS2 antibody immunoglobulin molecules of the invention (e.g., H1H7017N) may be inserted into a pET-based plasmid and expressed in the E. coli/T7 system. For example, the present invention includes methods for expressing an antibody or antigen-binding fragment thereof or immunoglobulin chain thereof in a host cell (e.g., bacterial host cell such as E. coli such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as an E. coli, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952, 496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-TMPRSS2 antigen-binding protein, such as an antibody or antigen-binding fragment thereof of the present invention, or an immunoglobulin chain thereof, comprising (i) introducing one or more polynucleotides (e.g., including the nucleotide sequence in any one or more of SEQ ID NOs: 1, 3, 5, 7, 9, 11, 13 or 15) encoding light and/or heavy immunoglobulin chains of the antigen-binding protein, e.g., H1H7017N or H4H7017N, for example, wherein the polynucleotide is in a vector; and/or integrated into a host cell chromosome and/or is operably linked to a promoter; (ii) culturing the host cell (e.g., CHO or Pichia or Pichia pastoris) under condition favorable to expression of the polynucleotide and, (iii) optionally, isolating the antigen-binding protein, (e.g., antibody or fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. For example, the present invention also includes anti-TMPRSS2 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 1 and a light chain immunoglobulin (or variable domain thereof or comprising the CDRs thereof) encoded by the nucleotide sequence set forth in SEQ ID NO: 3 which are the product of such production methods, and, optionally, the purification methods set forth herein. For example, in an embodiment of the invention, the product of the method is an anti-TMPRSS2 antigen-binding protein which is an antibody or fragment comprising a VH comprising the amino acid sequence set forth in SEQ ID NO: 2 and a VL comprising the amino acid sequence set forth in SEQ ID NO: 4; or comprising a HC comprising the amino acid sequence set forth in SEQ ID NO: 17 or 19 and a LC comprising the amino acid sequence set forth in SEQ ID NO: 18.

Eukaryotic and prokaryotic host cells, including mammalian cells, may be used as hosts for expression of an anti-TMPRSS2 antigen-binding protein. Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*. The present invention includes an isolated host cell (e.g., a CHO cell) comprising an antigen-binding protein, such as H1H7017N; or a polynucleotide encoding such a polypeptide thereof.

The term "specifically binds" refers to those antigen-binding proteins (e.g., mAbs) having a binding affinity to an antigen, such as TMPRSS2 protein (e.g., human TMPRSS2), expressed as KD, of at least about $10-8$ M (e.g., $2.81 \times 10-9$ M; $9.31 \times 10-9$M; $10-9$ M; $10-10$M, $10-11$ M, or $10-12$ M), as measured by real-time, label free bio-layer interferometry assay, for example, at 25° C. or 37° C., e.g., an Octet® HTX biosensor, or by surface plasmon resonance, e.g., BIACORE™, or by solution-affinity ELISA. The present invention includes antigen-binding proteins that specifically bind to TMPRSS2 protein.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., as defined in WO08/020079 or WO09/138519) (e.g., monovalent nanobodies, bivalent nanobodies, etc.), small modular immunopharmaceuticals (SMIPs), and shark variable IgNAR domains, are also encompassed within the expression "antigen-binding fragment," as used herein. In an embodiment of the invention, the antigen-binding fragment comprises three or more CDRs of H1H7017N (e.g., CDR-H1, CDR-H2 and CDR-H3; or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

Antigen-binding proteins (e.g., antibodies and antigen-binding fragments) may be mono-specific or multi-specific (e.g., bi-specific). Multispecific antigen-binding proteins are discussed further herein.

In specific embodiments, antibody or antibody fragments of the invention may be conjugated to a moiety such a ligand or a therapeutic moiety ("immunoconjugate"), such as an anti-viral drug, a second anti-influenza antibody, or any other therapeutic moiety useful for treating a viral infection, e.g., influenza viral infection. See below.

The present invention also provides a complex comprising an anti-TMPRSS2 antigen-binding protein, e.g., antibody or antigen-binding fragment, discussed herein complexed with TMPRSS2 polypeptide or an antigenic fragment thereof and/or with a secondary antibody or antigen-binding fragment thereof (e.g., detectably labeled secondary antibody) that binds specifically to the anti-TMPRSS2 antibody or fragment. In an embodiment of the invention, the antibody or fragment is in vitro (e.g., is immobilized to a solid substrate) or is in the body of a subject. In an embodiment of the invention, the TMPRSS2 is in vitro (e.g., is immobilized to a solid substrate) or is on the surface of a cell or is in the body of a subject. Immobilized anti-TMRPSS2 antibodies and antigen-binding fragments thereof which are covalently linked to an insoluble matrix material (e.g., glass or polysaccharide such as agarose or sepharose, e.g., a bead or other particle thereof) are also part of the present invention; optionally, wherein the immobilized antibody is complexed with TMPRSS2 or antigenic fragment thereof or a secondary antibody or fragment thereof.

"Isolated" antigen-binding proteins, antibodies or antigen-binding fragments thereof, polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The term "epitope" refers to an antigenic determinant (e.g., on TMPRSS2 polypeptide) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) (e.g., coversin) interacts is hydrogen/deuterium exchange detected by mass spectrometry. In general terms, the hydrogen/deuterium exchange method involves deuterium-labeling the protein of interest, followed by binding the antigen-binding protein, e.g., antibody or fragment or polypeptide, to the deuterium-labeled protein. Next, the TMPRSS2 protein/antigen-binding protein complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein (e.g., antibody or fragment or polypeptide), the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "competes" as used herein, refers to an antigen-binding protein (e.g., antibody or antigen-binding fragment thereof) that binds to an antigen (e.g., TMPRSS2) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. In an embodiment of the invention, competition between a first and second anti-TMPRSS2 antigen-binding protein (e.g., antibody) is determined by measuring the ability of an immobilized first anti-TMPRSS2 antigen-binding protein (e.g., antibody) (not initially complexed with TMPRSS2 protein) to bind to soluble TMPRSS2 protein complexed with a second anti-TMPRSS2 antigen-binding protein (e.g., antibody). A reduction in the ability of the first anti-TMPRSS2 antigen-binding protein (e.g., antibody) to bind to the complexed TMPRSS2 protein, relative to uncomplexed TMPRSS2 protein, indicates that the first and second anti-TMPRSS2 antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-TMPRSS2 antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-human TMPRSS2 monoclonal antibodies, the anti-TMPRSS2 mAb can be first captured onto anti-hFc antibody coated Octet biosensor tips (Pall ForteBio Corp., #18-5060) by submerging the tips into a solution of anti-human TMPRSS2 mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a co-complexed solution of human TMPRSS2 polypeptide and a second anti-human TMPRSS2 mAb (subsequently referred to as "mAb2"), that had been pre-incubated for a period of time and binding of mAb1 to the TMPRSS2 polypeptide can be determined. The biosensor tips can be washed in buffer in between every step of the experiment. The real-time binding response can be monitored during the course of the experiment and the binding response at the end of every step can be recorded.

For example, in an embodiment of the invention, the competition assay is conducted at 25° C. and pH about 7, e.g., 7.4, e.g., in the presence of buffer, salt, surfactant and a non-specific protein (e.g., bovine serum albumin).

Typically, an antibody or antigen-binding fragment of the invention which is modified in some way retains the ability to specifically bind to TMPRSS2, e.g., retains at least 10% of its TMPRSS2 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the TMPRSS2 binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., H1H7017N VH, VL, HC or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 4, 17, 18 or 19); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein (e.g., SEQ ID NO: 1 or 3); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

Anti-TMPRSS2 antigen-binding proteins, e.g., antibodies and antigen-binding fragments thereof of the present invention, in an embodiment of the invention, include a heavy chain immunoglobulin variable region having at least 70% (e.g., 80%, 85%, 90%, 95%, 99%) amino acid sequence identity to the amino acids set forth in SEQ ID NO: 2, 17 or 19; and/or a light chain immunoglobulin variable region having at least 70% (e.g., 80%, 85%, 90%, 95%, 99%) amino acid sequence identity to the amino acids set forth in SEQ ID NO: 4 or 18.

In addition, a variant anti-TMPRSS2 antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), nonsense mutations, deletions, or insertions. For example, the present invention includes antigen-binding proteins which include an immunoglobulin light chain variant comprising the amino acid sequence set forth in SEQ ID NO: 4 or 18 but having one or more of such mutations and/or an immunoglobulin heavy chain variant comprising the amino acid sequence set forth in SEQ ID NO: 2, 17 or 19 but having one or more of such mutations. In an embodiment of the invention, a variant anti-TMPRSS2 antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions).

The invention further provides variant anti-TMPRSS2 antigen-binding proteins, e.g., antibodies or antigen-binding fragments thereof, comprising one or more variant CDRs (e.g., any one or more of CDR-L1, CDR-L2, CDR-L3, CDR-H1, CDR-H2 and/or CDR-H3) that are set forth herein with at least 70%, 75%, 80%, 85%, 90%, 95%, 98%, 99% or 99.9% sequence identity or similarity to, e.g., SEQ ID NO: 12, 14, 16, 6, 8 and/or 10.

Embodiments of the present invention also include variant antigen-binding proteins, e.g., anti-TMPRSS2 antibodies and antigen-binding fragments thereof, that comprise immunoglobulin VHs and VLs; or HCs and LCs, which comprise an amino acid sequence having 70% or more (e.g., 80%, 85%, 90%, 95%, 97% or 99%) overall amino acid sequence identity or similarity to the amino acid sequences of the corresponding VHs, VLs, HCs or LCs specifically set forth herein, but wherein the CDR-L1, CDR-L2, CDR-L3, CDR-H1, CDR-H2 and CDR-H3 of such immunoglobulins are not variants and comprise the amino acid sequence set forth in SEQ ID NOs: 12, 14, 16, 6, 8 and 10, respectively. Thus, in such embodiments, the CDRs within variant antigen-binding proteins are not, themselves, variants.

Conservatively modified variant anti-TMPRSS2 antibodies and antigen-binding fragments thereof are also part of the present invention. A "conservatively modified variant" or a "conservative substitution" refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to significantly disrupt biological activity.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45.

Function-conservative variants of the anti-TMPRSS2 antibodies and antigen-binding fragments thereof are also part of the present invention. Any of the variants of the anti-TMPRSS2 antibodies and antigen-binding fragments thereof (as discussed herein) may be "function-conservative variants". Such function-conservative variants may, in some cases, also be characterized as conservatively modified variants. "Function-conservative variants," as used herein, refers to variants of the anti-TMPRSS2 antibodies or antigen-binding fragments thereof in which one or more amino acid residues have been changed without significantly altering one or more functional properties of the antibody or fragment. In an embodiment of the invention, a function-conservative variant anti-TMPRSS2 antibody or antigen-binding fragment thereof of the present invention comprises a variant amino acid sequence and exhibits one or more of the following functional properties:

Inhibits growth of influenza virus (e.g., A/Puerto Rico/ 08/1934 (H1N1)) in TMPRSS2-expressing cells (e.g., Calu-3 cells);
Binds to the surface of TMPRSS-expressing cells (e.g., MDCK/Tet-on), e.g., with an $EC_{50}$ value of 440 pM or 1.06 nM, respectively;
Does not significantly bind to MDCK/Tet-on cells which do not express TMPRSS2;
Binds to human TMPRSS2 with a $K_D$ of about $2.81 \times 10^{-9}$M at about 25° C.;
Binds to human TMPRSS2 with a $K_D$ of about $9.31 \times 10^{-9}$M at about 37° C.;
Binds to cynomolgus TMPRSS2 with a $K_D$ of about $5.60 \times 10^{-8}$ M at about 25° C.;
Binds to cynomolgus TMPRSS2 with a $K_D$ of about $1.40 \times 10^{-7}$M at about 37° C.;
Limits spread of influenza virus infection (e.g., by H1_PR34; H1_CA09; H1_Bris; H9N2 or H3N2 influenza virus) of cells, e.g., Calu-3, in vitro; and/or
Protects a mouse engineered to express the human TMPRSS2 protein from death caused by influenza virus infection, e.g., H1N1, or H3N2, for example, wherein the mice are infected with an otherwise lethal dose of the virus, optionally when combined with an anti-HA antibody.

The present invention includes a mouse engineered to express the human TMPRSS2 protein which includes, within the mouse's body, an anti-TMPRSS2 antigen-binding protein (e.g., antibody or antigen-binding fragment) such as H1H7017N and H4H7017N. See International patent application publication no. WO2017/151453.

A "neutralizing" or "antagonist" anti-TMPRSS2 antigen-binding protein, e.g., antibody or antigen-binding fragment, refers to a molecule that inhibits an activity of TMPRSS2 to any detectable degree, e.g., inhibits protease activity of TMPRSS2, for example, of a substrate such as HA; Cbz-Gly-Gly-Arg-AMC (Sigma), where Cbz is benzyloxycarbonyl and AMC is 7-amino-4-methylcoumarin; influenza virus HA0; coronavirus S protein; or precursor TMPRSS2 which is autocatalytically cleaved between Arg255 and Ile256 and/or inhibits influenza virus entry into a cell and/or inhibits influenza virus reproduction in the body of a subject.

"H1H7017N" and "H4H7017N" refer to antigen-binding proteins, such as antibodies and antigen-binding fragments thereof, that comprise the heavy chain or VH (or a variant thereof) and light chain or VL (or a variant thereof) as set forth below; or that comprise a VH that comprises the CDRs thereof (CDR-H1 (or a variant thereof), CDR-H2 (or a variant thereof) and CDR-H3 (or a variant thereof)) and a VL that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below.

In an embodiment of the invention, "H1H7017N" or "H4H7017N" refers to an antibody or antigen-binding fragment thereof comprising CDR-H1, CDR-H2, and CDR-H3 of an immunoglobulin heavy chain that comprises the amino acid sequence set forth in SEQ ID NO: 2, 17 or 19 and CDR-L1, CDR-L2, and CDR-L3 of an immunoglobulin light chain that comprises the amino acid sequence set forth in SEQ ID NO: 4 or 18.

In an embodiment of the invention, "H1H7017N" or "H4H7017N" refers to an antibody or antigen-binding fragment thereof comprising a VH that comprises the amino acid sequence set forth in SEQ ID NO: 2; and a VL that comprises the amino acid sequence set forth in SEQ ID NO: 4.

In an embodiment of the invention, "H1H7017N" refers to an antibody or antigen-binding fragment comprising a heavy chain immunoglobulin that comprises the amino acid sequence set forth in SEQ ID NO: 17; and a light chain immunoglobulin that comprises the amino acid sequence set forth in SEQ ID NO: 18.

In an embodiment of the invention, "H4H7017N" refers to an antibody or antigen-binding fragment comprising a heavy chain immunoglobulin that comprises the amino acid sequence set forth in SEQ ID NO: 19; and a light chain immunoglobulin that comprises the amino acid sequence set forth in SEQ ID NO: 18. The term "H4H7017N" also includes embodiments wherein the VH is fused to a wild-type IgG4, e.g., wherein residue 108 is S.

Anti-TMRPS22 Antibody or Antigen-Binding Fragment
H1H7017N and H4H7017NH1H7017N and H4H7017N Heavy
Chain Variable Region (DNA)
(SEQ ID NO: 1)
CAGGTGCAGCTGGTGGAGTCTGGGGGAGGCGTGGTCCAGCCTGGAGGTC

CCTGAGACTCTCCTGTGCAGCGTCTGGATTCACCTTCAGTTCCTATGGCA

TGCACTGGGTCCGCCAGTCTCCAGGCAAGGGGCTCGAGTGGGTGGCAGTT

ATATGGAATGATGGAAGTTATGTATACTATGCAGACTCCGTGAAGGGCCG

ATTCACCATCTCCAGAGACATTTCCAAGAACACGCTGTTTCTGCAAATGA

ACAGCCTGAGAGCCGAGGACACGGCTGTGTATTACTGTGCGAGAGAGGGG

GAGTGGGTACTTTACTACTTTGACTACTGGGGCCAGGGAACCCTGGTCAC

CGTCTCCTCA

H1H7017N and H4H7017N Heavy Chain Variable Region
(Polypeptide)
(SEQ ID NO: 2)
QVQLVESGGGVVQPGRSLRLSCAA<u>SGFTFSSYG</u>MHWVRQSPGKGLEWVAV <u>IWNDGSYV</u>YYADSVKGRFTISRDISKNTLFLQMNSLRAEDTAVYYC<u>AREG</u>

<u>EWVLYYFDY</u>WGQGTLVTVSS

H1H7017N and H4H7017N Light Chain Variable Region
(DNA)
(SEQ ID NO: 3)
GACATCCAGATGACCCAGTCTCCTTCCACCCTGTCTGCATCTGTTGGAGA

CAGAGTCACCATCACTTGCCGGGCCAGTCAGAGTATTAGTAGCTGGTTGG

CCTGGTATCAGCAGAAACCAGGGAAAGCCCCTAAACTCCTGATCTATAAG

GCGTCTACTTTAGAAAGTTGGGTCCCATCAAGGTTCAGCGGCAGTGGATC

TGGGACAGAATTCACTCTCACCATCAGCAGCCTGCAGCCTGATGATTTTG

CAACTTATTACTGCCAACAGTATAATAGTTATTCGTACACTTTTGGCCAG

GGGACCAAGCTGGAGATCAAA

H1H7017N and H4H7017N Light Chain Variable Region
(Polypeptide)
(SEQ ID NO: 4)
DIQMTQSPSTLSASVGDRVTITCRAS<u>QSISSW</u>LAWYQQKPGKAPKLLIY<u>K</u>

<u>AS</u>TLESGVPSRFSGSGSGTEFTLTISSLQPDDFATYYC<u>QQYNSYSYT</u>FGQ

GTKLEIK

H1H7017N and H4H7017N CDR-H1 (DNA)
(SEQ ID NO: 5)
GGA TTC ACC TTC AGT TCC TAT GGC H1H7017N and H4H7017N CDR-H1 (Polypeptide)
(SEQ ID NO: 6)
G F T F S S Y G
(or a variant thereof having 1, 2, 3 or 4 point mutations and/or point deletions)

H1H7017N and H4H7017N CDR-H2 (DNA)
(SEQ ID NO: 7)
ATA TGG AAT GAT GGA AGT TAT GTA H1H7017N and H4H7017N CDR-H2 (Polypeptide)
(SEQ ID NO: 8)
I W N D G S Y V
(or a variant thereof having 1, 2, 3 or 4 point mutations and/or point deletions)

H1H7017N and H4H7017N CDR-H3 (DNA)
(SEQ ID NO: 9)
GCG AGA GAG GGG GAG TGG GTA CTT TAC TAC TTT GAC

TAC

H1H7017N and H4H7017N CDR-H3 (Polypeptide)
(SEQ ID NO: 10)
A R E G E W V L Y Y F D Y
(or a variant thereof having 1, 2, 3 or 4 point mutations and/or point deletions))

H1H7017N and H4H7017N CDR-L1 (DNA)
(SEQ ID NO: 11)
CAG AGT ATT AGT AGC TGG

H1H7017N and H4H7017N CDR-L1 (Polypeptide)
(SEQ ID NO: 12)
Q S I SS W
(or a variant thereof having 1, 2, 3 or 4 point mutations and/or point deletions)

H1H7017N and H4H7017N CDR-L2 (DNA)
(SEQ ID NO: 13)
AAG GCG TCT

H1H7017N and H4H7017N CDR-L2 (Polypeptide)
(SEQ ID NO: 14)
K A S
(or a variant thereof having a point mutation and/or point deletion))

H1H7017N and H4H7017N CDR-L3 (DNA)
(SEQ ID NO: 15)
CAA CAG TAT AAT AGT TAT TCG TAC ACT H1H7017N and H4H7017N CDR-L3 (Polypeptide)
(SEQ ID NO: 16)
Q Q Y N S Y S Y T
(or a variant thereof having 1, 2, 3 or 4 point mutations and/or point deletions)

H1H7017N
Full length heavy chain-human IgG1
(SEQ ID NO: 17)
QVQLVESGGGVVQPGRSLRLSCAASGFTFSSYGMHWVRQSPGKGLEWVAV

IWNDGSYVYYADSVKGRFTISRDISKNTLFLQMNSLRAEDTAVYYCAREG

EWVLYYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

```
-continued
YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Full length light chain-human Kappa
                                         (SEQ ID NO: 18)
DIQMTQSPSTLSASVGDRVTITCRASQSISSWLAWYQQKPGKAPKLLIYK

ASTLESGVPSRFSGSGSGTEFTLTISSLQPDDFATYYCQQYNSYSYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

H4H7017N
Full length heavy chain-human IgG4 (S108P)
                                         (SEQ ID NO: 19)
QVQLVESGGGVVQPGRSLRLSCAASGFTFSSYGMHWVRQSPGKGLEWVAV

IWNDGSYVYYADSVKGRFTISRDISKNTLFLQMNSLRAEDTAVYYCAREG

EWVLYYFDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

Full length light chain-human Kappa
                                         (SEQ ID NO: 18)
DIQMTQSPSTLSASVGDRVTITCRASQSISSWLAWYQQKPGKAPKLLIYK

ASTLESGVPSRFSGSGSGTEFTLTISSLQPDDFATYYCQQYNSYSYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Antibodies and antigen-binding fragments of the present invention comprise immunoglobulin chains including the amino acid sequences set forth herein as well as cellular and in vitro post-translational modifications to the antibody. For example, the present invention includes antibodies and antigen-binding fragments thereof that specifically bind to TMPRSS2 comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present invention provides a vessel (e.g., a plastic or glass vial, e.g., with a cap or a chromatography column, hollow bore needle or a syringe cylinder) comprising an anti-TMPRSS2 antigen-binding protein of the present invention, e.g., H1H7017N or H4H7017N.

The present invention also provides an injection device comprising one or more antigen-binding proteins (e.g., antibody or antigen-binding fragment) that bind specifically to TMPRSS2, e.g., H4H7017N or H1H7017N, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antigen-binding protein, e.g., an antibody or antigen-binding fragment thereof, from a combination of the present invention, or a pharmaceutical composition thereof is an intravenous (IV) injection device. Such a device can include the antigen-binding protein or a pharmaceutical composition thereof in a cannula or trocar/needle which may be attached to a tube which may be attached to a bag or reservoir for holding fluid (e.g., saline) introduced into the body of the subject through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a subject's body. External infusion pumps are medical devices that deliver the antibody or fragment or a pharmaceutical composition thereof into a subject's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The present invention further provides methods for administering an anti-TMPRSS2 antigen-binding protein of the present invention, e.g., H4H7017N or H1H7017N, comprising introducing the antigen-binding protein into the body of a subject (e.g., a human). For example, the method comprises piercing the body of the subject with a needle of a syringe and injecting the antigen-binding protein into the body of the subject, e.g., into the vein, artery, tumor, muscular tissue or subcutis of the subject.

Preparation of Human Antibodies

Methods for generating human antibodies in transgenic mice are known in the art. Any such known methods can be used in the context of the present invention to make human antibodies that specifically bind to TMPRSS2. An immunogen comprising any one of the following can be used to generate antibodies to TMPRSS2. In certain embodiments of the invention, the antibodies of the invention are obtained from mice immunized with a full length, native TMPRSS2, or with a live attenuated or inactivated virus, or with DNA encoding the protein or fragment thereof. Alternatively, the TMPRSS2 protein or a fragment thereof may be produced using standard biochemical techniques and modified and used as immunogen. In one embodiment of the invention, the immunogen is a recombinantly produced TMPRSS2 protein or fragment thereof. In certain embodiments of the invention, the immunogen may be a TMPRSS2 polypeptide vaccine. In certain embodiments, one or more booster injections may be administered. In certain embodiments, the immunogen may be a recombinant TMPRSS2 polypeptide expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to TMPRSS2 can be initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-TMPRSS2 Antibodies Comprising Fc Variants

According to certain embodiments of the present invention, anti-TMPRSS2 antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-TMPRSS2 antibodies comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434I/]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-TMPRSS2 antigen-binding proteins, e.g., antibodies or antigen-binding fragments, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-TMPRSS antigen-binding proteins, e.g., antibodies and antigen-binding fragments thereof, that comprise a VH and/or VL as set forth herein comprising any possible combinations of the foregoing Fc domain mutations, are contemplated within the scope of the present invention.

The present invention also includes anti-TMPRSS2 antigen-binding proteins, antibodies or antigen-binding fragments, comprising a VH set forth herein and a chimeric heavy chain constant (CH) region, wherein the chimeric CH region comprises segments derived from the CH regions of more than one immunoglobulin isotype. For example, the antibodies of the invention may comprise a chimeric CH region comprising part or all of a CH2 domain derived from a human IgG1, human IgG2 or human IgG4 molecule, combined with part or all of a CH3 domain derived from a human IgG1, human IgG2 or human IgG4 molecule. According to certain embodiments, the antibodies of the invention comprise a chimeric CH region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric CH region as described herein may, in certain embodiments, exhibit modified Fc effector functions without adversely affecting the therapeutic or pharmacokinetic properties of the antibody. (See, e.g., WO2014/022540).

Immunoconjugates

The invention encompasses an anti-TMPRSS2 antigen-binding proteins, e.g., antibodies or antigen-binding fragments, conjugated to another moiety, e.g., a therapeutic moiety (an "immunoconjugate"), such as a toxoid or an anti-viral drug to treat influenza virus infection. In an embodiment of the invention, an anti-TMPRSS2 antibody or fragment is conjugated to any of the further therapeutic agents set forth herein. As used herein, the term "immunoconjugate" refers to an antigen-binding protein, e.g., an antibody or antigen-binding fragment, which is chemically or biologically linked to a radioactive agent, a cytokine, an interferon, a target or reporter moiety, an enzyme, a peptide or protein or a therapeutic agent. The antigen-binding protein may be linked to the radioactive agent, cytokine, interferon, target or reporter moiety, enzyme, peptide or therapeutic agent at any location along the molecule so long as it is able to bind its target (TMPRSS2). Examples of immunoconjugates include antibody-drug conjugates and antibody-toxin fusion proteins. In one embodiment of the invention, the agent may be a second, different antibody that binds specifically to TMPRSS2. The type of therapeutic moiety that may be conjugated to the anti-TMPRSS2 antigen-binding protein (e.g., antibody or fragment) will take into account the condition to be treated and the desired therapeutic effect to be achieved. See, e.g., Arnon et al., "Monoclonal Antibodies For Immunotargeting Of Drugs In Cancer Therapy", Monoclonal Antibodies And Cancer Therapy, Reisfeld et al. (eds.), pp. 243-56 (Alan R. Liss, Inc. 1985); Hellstrom et al., "Antibodies For Drug Delivery", Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", Monoclonal Antibodies 1984: Biological And Clinical Applications, Pinchera et al. (eds.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Multi-Specific Antibodies

The present invention includes anti-TMPRSS2 antigen-binding proteins, e.g., antibodies and antigen-binding fragments thereof, as well as methods of use thereof and methods of making such antigen-binding proteins. The term "anti-TMPRSS2" antigen-binding proteins, e.g., antibodies or antigen-binding fragments, includes multispecific (e.g., bispecific or biparatopic) molecules that include at least one first antigen-binding domain that specifically binds to TMPRSS2 (e.g., an antigen-binding domain from H1H7017N or H4H7017N) and at least one second antigen-binding domain that binds to a different antigen or to an epitope in TMPRSS2 which is different from that of the first antigen-binding domain (e.g., influenza HA such as an antigen-binding domain from H1H14611N2, H1H14612N2 or H1H11729P). In an embodiment of the invention, the first and second epitopes overlap. In another embodiment of the invention, the first and second epitopes do not overlap. For example, in an embodiment of the invention, a multispecific antibody is a bispecific IgG antibody (e.g., IgG1 or IgG4) that includes a first antigen-binding domain that binds specifically to TMPRSS2 including the heavy and light immunoglobulin chain of H1H7017N or H4H7017N, and a second antigen-binding domain that binds specifically to influenza HA (comprising a different light and heavy immunoglobulin chain such as from H1H14611N2, H1H14612N2 or H1H11729P).

"H1H7017N" includes a multispecific molecules, e.g., antibodies or antigen-binding fragments, that include the HCDRs and LCDRs, VH and VL, or HC and LC of H1H7017N (including variants thereof as set forth herein).

"H4H7017N" includes a multispecific molecules, e.g., antibodies or antigen-binding fragments, that include the HCDRs and LCDRs, VH and VL, or HC and LC of H4H7017N (including variants thereof as set forth herein).

In an embodiment of the invention, an antigen-binding domain that binds specifically to TMPRSS, which may be included in a multispecific molecule, comprises:

(1)
(i) a heavy chain variable domain sequence that comprises CDR-H1 comprising the amino acid sequence set forth in SEQ ID NO: 6, CDR-H2 comprising the amino acid sequence set forth in SEQ ID NO: 8, and CDR-H3 comprising the amino acid sequence set forth in SEQ ID NO: 10, and (ii) a light chain variable domain sequence that comprises CDR-L1 comprising the amino acid sequence set forth in SEQ ID NO: 12, CDR-L2 comprising the amino acid sequence set forth in SEQ ID NO: 14, and CDR-L3 comprising the amino acid sequence set forth in SEQ ID NO: 16; or, (2)
(i) a heavy chain variable domain sequence comprising the amino acid sequence set forth in SEQ ID NO: 2, and
(ii) a light chain variable domain sequence comprising the amino acid sequence set forth in SEQ ID NO: 4; or, (3)
(i) a heavy chain immunoglobulin sequence comprising the amino acid sequence set forth in SEQ ID NO: 17 or 19, and
(ii) a light chain immunoglobulin sequence comprising the amino acid sequence set forth in SEQ ID NO: 18.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In an embodiment of the invention, a multispecific molecule comprises, in addition to an antigen-binding site that bind specifically to TMPRSS2, an antigen-binding site that binds specifically to influenza HA taken from an antibody selected from the group consisting of:

H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B;

H1H17956B; H1H17957B; H1H17958B; H1H17959B;
H1H17960B; H1H17961B; H1H17962B; H1H17963B;
H1H17964B; H1H17965B; H1H17966B; H1H17967B;
H1H17968B; H1H17969B; H1H17970B; H1H17971B;
H1H17972B; H1H17973B; H1H17974B; H1H17975B;
H1H17976B; H1H17977B; H1H17978B; H1H17979B;
H1H17980B; H1H17981B; H1H17982B; H1H17983B;
H1H17984B; H1H17985B; H1H17986B; H1H17987B;
H1H17988B; H1H17989B; H1H17990B; H1H17991B;
H1H17992B; H1H17993B; H1H17994B; H1H17995B;
H1H17996B; H1H17997B; H1H17998B; H1H17999B;
H1H18000B; H1H18001B; H1H18002B; H1H18003B;
H1H18004B; H1H18005B; H1H18006B; H1H18007B;
H1H18008B; H1H18009B; H1H18010B; H1H18011B;
H1H18012B; H1H18013B; H1H18014B; H1H18015B;
H1H18016B; H1H18017B; H1H18018B; H1H18019B;
H1H18020B; H1H18021B; H1H18022B; H1H18023B;
H1H18024B; H1H18025B; H1H18026B; H1H18027B;
H1H18028B; H1H18029B; H1H18030B; H1H18031B;
H1H18032B; H1H18033B; H1H18034B; H1H18035B;
H1H18037B; H1H18038B; H1H18039B; H1H18040B;
H1H18041B; H1H18042B; H1H18043B; H1H18044B;
H1H18045B; H1H18046B; H1H18047B; H1H18048B;
H1H18049B; H1H18051B; H1H18052B; H1H18053B;
H1H18054B; H1H18055B; H1H18056B; H1H18057B;
H1H18058B; H1H18059B; H1H18060B; H1H18061B;
H1H18062B; H1H18063B; H1H18064B; H1H18065B;
H1H18066B; H1H18067B; H1H18068B; H1H18069B;
H1H18070B; H1H18071B; H1H18072B; H1H18073B;
H1H18074B; H1H18075B; H1H18076B; H1H18077B;
H1H18078B; H1H18079B; H1H18080B; H1H18081B;
H1H18082B; H1H18083B; H1H18084B; H1H18085B;
H1H18086B; H1H18087B; H1H18088B; H1H18089B;
H1H18090B; H1H18091B; H1H18092B; H1H18093B;
H1H18094B; H1H18095B; H1H18096B; H1H18097B;
H1H18098B; H1H18099B; H1H18100B; H1H18101B;
H1H18102B; H1H18103B; H1H18104B; H1H18105B;
H1H18107B; H1H18108B; H1H18109B; H1H18110B;
H1H18111B; H1H18112B; H1H18113B; H1H18114B;
H1H18115B; H1H18116B; H1H18117B; H1H18118B;
H1H18119B; H1H18120B; H1H18121B; H1H18122B;
H1H18123B; H1H18124B; H1H18125B; H1H18126B;
H1H18127B; H1H18128B; H1H18129B; H1H18130B;
H1H18131B; H1H18132B; H1H18133B; H1H18134B;
H1H18135B; H1H18136B; H1H18137B; H1H18138B;
H1H18139B; H1H18140B; H1H18141B; H1H18142B;
H1H18143B; H1H18144B; H1H18145B; H1H18146B;
H1H18147B; H1H18148B; H1H18149B; H1H18150B;
H1H18151B; H1H18152B; H1H18153B; H1H18154B;
H1H18155B; H1H18156B; H1H18157B; H1H18158B;
H1H18159B; H1H18160B; H1H18161B; H1H18162B;
H1H18163B; H1H18164B; H1H18165B; H1H18166B;
H1H18167B; H1H18168B; H1H18169B; H1H18170B;
H1H18171B; H1H18172B; H1H18173B; H1H18174B;
H1H18175B; H1H18176B; H1H18177B; H1H18178B;
H1H18179B; H1H18180B; H1H18181B; H1H18182B;
H1H18183B; H1H18184B; H1H18185B; H1H18186B;
H1H18187B; H1H18188B; H1H18189B; H1H18190B;
H1H18191B; H1H18192B; H1H18193B; H1H18194B;
H1H18195B; H1H18196B; H1H18197B; H1H18198B;
H1H18199B; H1H18200B; H1H18201B; H1H18202B;
H1H18203B; H1H18204B; H1H18205B; H1H18206B;
H1H18207B; H1H18208B; H1H18209B; H1H18210B;
H1H18211B; H1H18212B; H1H18213B; H1H18214B;
H1H18216B; H1H18217B; H1H18218B; H1H18219B;
H1H18220B; H1H18221B; H1H18222B; H1H18223B;
H1H18224B; H1H18225B; H1H18226B; H1H18227B;
H1H18228B; H1H18229B; H1H18230B; H1H18231B;
H1H18232B; H1H18233B; H1H18234B; H1H18235B;
H1H18236B; H1H18237B; H1H18238B; H1H18239B;
H1H18240B; H1H18241B; H1H18242B; H1H18243B;
H1H18244B; H1H18245B; H1H18246B; H1H18247B;
H1H18248B; H1H18249B; H1H18250B; H1H18251B;
H1H18252B; H1H18253B; H1H18254B; H1H18255B;
H1H18256B; H1H18257B; H1H18258B; H1H18259B;
H1H18261B; H1H18262B; H1H18263B; H1H18264B;
H1H18265B; H1H18266B; H1H18267B; H1H18268B;
H1H18269B; H1H18270B; H1H18271B; H1H18272B;
H1H18274B; H1H18275B; H1H18276B; H1H18277B;
H1H18278B; H1H18279B; H1H18280B; H1H18281B;
H1H18282B; H1H18283B; H1H18284B; H1H18285B;
H1H18286B; H1H18287B; H1H18288B; H1H18289B;
H1H18290B; H1H18291B; H1H18292B; H1H18293B;
H1H18294B; H1H18295B; H1H18297B; H1H18298B;
H1H18299B; H1H18300B; H1H18301B; H1H18302B;
H1H18303B; H1H18304B; H1H18305B; H1H18306B;
H1H18307B; H1H18308B; H1H18309B; H1H18310B;
H1H18311B; H1H18312B; H1H18313B; H1H18314B;
H1H18315B; H1H18316B; H1H18317B; H1H18318B;
H1H18319B; H1H18320B; H1H18321B; H1H18322B;
H1H18323B; H1H18324B; H1H18325B; H1H18326B;
H1H18327B; H1H18328B; H1H18329B; H1H18330B;
H1H18331B; H1H18332B; H1H18333B; H1H18334B; and
H1H18335B; as set forth in International patent application publication no. WO2016/100807 (e.g., the CDR-Hs, VH or heavy chain thereof; and the CDR-Ls, VL or light chain thereof).

In an embodiment of the invention, a multispecific molecule comprises, in addition to an antigen-binding site that binds specifically to TMPRSS2, an antigen-binding site that binds specifically to influenza Group II HA protein, e.g., which comprises VH and VL of H1H14611N2 (e.g., SEQ ID Nos: 24 and 28); or a heavy chain immunoglobulin comprising CDR-H1, CDR-H2 and CDR-H3 of H1H14611N2 (e.g., SEQ ID NOs: 25-27) and a light chain immunoglobulin comprising CDR-L1, CDR-L2 and CDR-L3 of H1H14611N2 (e.g., SEQ ID NOs: 29-31).

In an embodiment of the invention, a multispecific molecule comprises, in addition to an antigen-binding site that bind specifically to TMPRSS2, an antigen-binding site that binds specifically to influenza Group II HA protein, e.g., which comprises $V_H$ and $V_L$ of H1H14612N2 (e.g., SEQ ID Nos: 40 and 44); or a heavy chain immunoglobulin comprising CDR-H1, CDR-H2 and CDR-H3 of H1H14612N2 (e.g., SEQ ID NOs: 41-43) and a light chain immunoglobulin comprising CDR-L1, CDR-L2 and CDR-L3 of H1H14612N2 (e.g., SEQ ID NOs: 45-47).

In an embodiment of the invention, a multispecific molecule comprises, in addition to an antigen-binding site that bind specifically to TMPRSS2, an antigen-binding site that binds specifically to influenza Group I HA protein, e.g., which comprises $V_H$ and $V_L$ of H1H11729P (e.g., SEQ ID Nos: 32 and 36); or a heavy chain immunoglobulin comprising CDR-H1, CDR-H2 and CDR-H3 of H1H11729P (e.g., SEQ ID NOs: 33-35) and a light chain immunoglobulin comprising CDR-L1, CDR-L2 and CDR-L3 of H1H11729P (e.g., SEQ ID NOs: 37-39).

In one embodiment of the invention, a bispecific antigen-binding fragment comprises a first scFv (e.g., comprising VH and VL of H1H7017N or H4H7017N) having binding specificity for a first epitope (e.g., TMPRSS2) and a second scFv (e.g., comprising VH and $V_L$ of an anti-influenza HA antibody) having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 48) wherein n is, for example, 1, 2, 3, 4, 5, 6, 7, 8, 9 or 10). Other bispecific antigen-binding fragments include an F(ab)$_2$ of a bispecific IgG antibody which comprises the heavy and light chain CDRs of H1H7017N or H4H7017N and of another antibody that binds to a different epitope.

Therapeutic Methods

The present invention provides methods for treating or preventing viral infection or cancer (e.g., prostate cancer) by administering a therapeutically effective amount of anti-TMPRSS2 antigen-binding protein, e.g., antibody or antigen-binding fragment, (e.g., H1H7017N or H4H7017N) to a subject (e.g., a human) in need of such treatment or prevention.

Influenza virus infection may be treated or prevented, in a subject, by administering an anti-TMPRSS2 antigen-binding protein of the present invention to a subject. The influenza viruses are classified into types A, B and C on the basis of their core proteins. The subtypes of influenza A viruses are determined by envelope glycoproteins possessing either hemagglutinin (HA) or neuraminidase (NA) activity. There are several HA subtypes (e.g., HA1, HA2, HA3, HA4, HA5, HA6, HA7, HA8, HA9, HA10, HA11, HA12, HA13, HA14, HA15, HA16, HA17 or HA18—these subtypes may be designated as H1, H2, H3, etc.) and NA subtypes (e.g., NA1, NA2, NA3, NA4, NA5, NA6, NA7, NA8, NA9, NA10 or NA11—these subtypes may be designated as N1, N2, N3, etc.) of influenza A viruses which are used to designate influenza A subtype. For example, Influenza A virus H1N1 and H3N2 are commonly known human pathogens. Humans are commonly infected by viruses of the subtypes H1, H2 or H3, and N1 or N2. The present invention includes methods for treating or preventing infection with an influenza virus subtype discussed herein. Multispecific antibodies and antigen-binding fragments thereof that bind to TMPRSS2, in an embodiment of the invention, also bind to HA/and/or to NA, e.g., of a subtype set forth herein.

An effective or therapeutically effective dose of anti-TMPRSS2 antigen-binding protein, e.g., antibody or antigen-binding fragment (e.g., H1H7017N or H4H7017N), for treating or preventing a viral infection refers to the amount of the antibody or fragment sufficient to alleviate one or more signs and/or symptoms of the infection in the treated subject, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of antibody or antigen-binding fragment thereof of the present invention, for treating or preventing viral infection, e.g., in an adult human subject, is about 0.01 to about 200 mg/kg, e.g., up to about 150 mg/kg. In an embodiment of the invention, the dosage is up to about 10.8 or 11 grams (e.g., about 1, 2, 3, 4, 5, 6, 7, 8, 9, 10 or 11 grams). Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of a disease or disorder such as viral infection or cancer. The subject may have a viral infection, e.g., an influenza infection, or be predisposed to developing an infection. Subjects predisposed to developing an infection, or subjects who may be at elevated risk for contracting an infection (e.g., of influenza virus), include subjects with compromised immune systems because of autoimmune disease, subjects receiving immunosuppressive therapy (for example, following organ transplant), subjects afflicted with human immunodeficiency syndrome (HIV) or acquired immune deficiency syndrome (AIDS), subjects with forms of anemia that deplete or destroy white blood cells, subjects receiving radiation or chemotherapy, or subjects afflicted with an inflammatory disorder. Additionally, subjects of very young (e.g., 5 years of age or younger) or old age (e.g., 65 years of age or older) are at increased risk. Moreover, a subject may be at risk of contracting a viral infection due to proximity to an outbreak of the disease, e.g. subject resides in a densely-populated city or in close proximity to subjects having confirmed or suspected infections of a virus, or choice of employment, e.g. hospital worker, pharmaceutical researcher, traveler to infected area, or frequent flier.

"Treat" or "treating" means to administer an anti-TMPRSS2 antigen-binding protein, e.g., antibody or antigen-binding fragment of the present invention (e.g., H1H7017N or H4H7017N), to a subject having one or more signs or symptoms of a disease or infection, e.g., viral infection, for which the antigen-binding protein is effective when administered to the subject at an effective or therapeutically effective amount or dose (as discussed herein).

The present invention also encompasses prophylactically administering an anti-TMPRSS2 antigen-binding protein, e.g., antibody or antigen-binding fragment thereof of the present invention (e.g., H1H7017N or H4H7017N), to a subject who is at risk of viral infection so as to prevent such infection. Passive antibody-based immunoprophylaxis has proven an effective strategy for preventing subject from viral infection. See e.g., Berry et al., Passive broad-spectrum influenza immunoprophylaxis. Influenza Res Treat. 2014; 2014:267594. Epub 2014 Sep. 22; and Jianqiang et al., Passive immune neutralization strategies for prevention and control of influenza A infections, Immunotherapy. 2012 February; 4(2): 175-186; Prabhu et al., Antivir Ther. 2009; 14(7):911-21, Prophylactic and therapeutic efficacy of a chimeric monoclonal antibody specific for H5 hemagglutinin against lethal H5N1 influenza. "Prevent" or "preventing" means to administer an anti-TMPRSS2 antigen-binding protein, e.g., antibody or antigen-binding fragment of the present invention (e.g., H1H7017N or H4H7017N), to a subject to inhibit the manifestation of a disease or infection (e.g., viral infection) in the body of a subject, for which the antigen-binding protein is effective when administered to the subject at an effective or therapeutically effective amount or dose (as discussed herein).

In an embodiment of the invention, a sign or symptom of a viral infection in a subject is survival or proliferation of virus in the body of the subject, e.g., as determined by viral titer assay (e.g., influenza virus propagation in embryonated chicken eggs or influenza virus hemagglutination assay). Other signs and symptoms of viral infection are discussed herein.

The present invention provides a method for treating or preventing viral infection (e.g., influenza virus or corona virus infection) or for inducing the regression or elimination or inhibiting the progression of at least one sign or symptom of viral infection such as:
Fever or feeling feverish/chills;
Cough;
Sore throat;
Runny or stuffy nose;
Sneezing;
Muscle or body aches;
Headaches;
Fatigue (tiredness);
vomiting;
diarrhea;
respiratory tract infection;
chest discomfort;
shortness of breath;
bronchitis; and/or
pneumonia,
which sign or symptom is secondary to viral infection, in a subject in need thereof (e.g., a human), by administering a therapeutically effective amount of anti-TMPRSS2 antigen-binding protein (e.g., H1H7017N or H4H7017N) to the subject, for example, by injection of the protein into the body of the subject.

The present invention also includes methods for treating or preventing cancer, e.g., metastatic cancer, e.g., prostate cancer (e.g., which is characterized by expression of a TMPRSS2:ERG fusion), colon cancer, lung cancer, pancreas cancer, urinary tract cancer, breast cancer, ovarian cancer, prostate adenocarcinoma, renal cell carcinoma, colorectal adenocarcinoma, lung adenocarcinoma, lung squamous cell carcinoma and/or pleural mesothelioma, in a subject, by administering a therapeutically effective amount of TMPRSS2 antigen-binding protein (e.g., H1H7017N or H4H7017N) to the subject, for example, by injection of the protein into the body of the subject. In an embodiment of the invention, the subject is also administered the TMPRSS2 antigen-binding protein in association with a further therapeutic agent, for example, an anti-cancer therapeutic agent. In an embodiment of the invention, the cancer is a tumor whose cells express TMPRSS2 or a variant thereof.

Combinations and Pharmaceutical Compositions

To prepare pharmaceutical compositions of the anti-TMPRSS2 antigen-binding proteins, e.g., antibodies and antigen-binding fragments thereof (e.g., H1H7017N or H4H7017N), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

The scope of the present invention includes desiccated, e.g., freeze-dried, compositions comprising an anti-TMPRSS2 antigen-binding proteins, e.g., antibody or antigen-binding fragment thereof (e.g., H1H7017N or H4H7017N), or a pharmaceutical composition thereof that includes a pharmaceutically acceptable carrier but substantially lacks water.

In a further embodiment of the invention, a further therapeutic agent that is administered to a subject in association with an anti-TMPRSS2 antigen-binding protein, e.g., antibody or antigen-binding fragment thereof (e.g., H1H7017N or H4H7017N), disclosed herein is administered to the subject in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-TMPRSS2 antigen-binding protein, e.g., antibody or antigen-binding fragment thereof (e.g., H1H7017N or H4H7017N), comprising introducing the protein into the body of a subject. For example, the method comprises piercing the body of the subject with a needle of a syringe and injecting the antigen-binding protein into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-TMPRSS2 antigen-binding proteins, e.g., antibodies or antigen-binding fragments thereof (e.g., H1H7017N or H4H7017N), polypeptides (e.g., an HC, LC, VH or VL of H1H7017N or H4H7017N) or polynucleotides or vectors set forth herein or a pharmaceutical composition thereof comprising a pharmaceutically acceptable carrier.

In an embodiment of the invention, an anti-TMPRSS2 antigen-binding protein, e.g., antibody or antigen-binding fragment thereof of the present invention (e.g., H1H7017N or H4H7017N), is in association with one or more further therapeutic agents. For example, in an embodiment of the invention, the further therapeutic agent is an anti-viral drug and/or a vaccine. As used herein, the term "anti-viral drug" refers to any anti-infective drug or therapy used to treat, prevent, or ameliorate a viral infection in a subject. The term "anti-viral drug" includes, but is not limited to a cationic steroid antimicrobial, leupeptin, aprotinin, amantadine, rimantadine, oseltamivir, zanamivir, ribavirin, or interferon-alpha2b. Methods for treating or preventing virus (e.g., influenza) infection in a subject in need of said treatment or prevention by administering H1H7017N or H4H7017N in association with a further therapeutic agent are part of the present invention.

For example, in an embodiment of the invention, the further therapeutic agent is a vaccine, e.g., an influenza vaccine. In an embodiment of the invention, a vaccine is an inactivated/killed virus vaccine, a live attenuated virus vaccine or a virus subunit vaccine.

For example, in an embodiment of the invention, the further therapeutic agent is:

(polyamide). See Shen et al. Biochimie 142: 1-10 (2017).

In an embodiment of the invention, the anti-viral drug is an antibody or antigen-binding fragment that binds specifically to influenza virus, e.g., influenza HA. For example, in an embodiment of the invention, the anti-HA antibody is any one of H1H14611N2; H1H14612N2; H1H11723P;

H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; or H1H18335B; as set forth in International patent application publication no. WO2016/100807; or an antigen-binding fragment thereof, e.g., wherein the antibody or fragment comprises a light chain immunoglobulin that includes CDR-L1, CDR-L2 and CDR-L3 (e.g., the VL or light chain thereof); and a heavy chain that includes CDR-H1, CDR-H2 and CDR-H3 (e.g., the VH or heavy chain thereof) of any of the foregoing anti-influenza HA antibodies.

In an embodiment of the invention, a further therapeutic agent is an antibody or antigen-binding fragment that binds to influenza Group II HA protein such as H1H14611N2; or an antibody or fragment that comprises VH and VL of H1H14611N2; or a heavy chain immunoglobulin comprising CDR-H1, CDR-H2 and CDR-H3 of H1H14611N2 (e.g., SEQ ID NOs: 25-27) and a light chain immunoglobulin comprising CDR-L1, CDR-L2 and CDR-L3 of H1H14611N2 (e.g., SEQ ID NOs: 29-31). "H1H14611N2" refers to any anti-group II HA antibody comprising such sequences.

H1H14611N2
Heavy chain variable region
(SEQ ID NO: 24)
EVQLVESGGGLVKPGGSLRLSCAAS<u>GFTFSGFS</u>MNWVRQVPGKGLEWVSS<u>ISTSGNYM</u>YYADSVKGRFTISRDNAKKSFSLQMNSLRAEDSAIYYC<u>ARGGGYNWNLFDY</u>WGQGSLVTVSS

CDR-H1:
(SEQ ID NO: 25)
GFTFSGFS

CDR-H2:
(SEQ ID NO: 26)
ISTSGNYM

CDR-H3:
(SEQ ID NO: 27)
ARGGGYNWNLFDY

Light chain variable region
(SEQ ID NO: 28)
EIVLTQSPOTLSLSPGERATLSCRAS<u>QSLNSNY</u>LAWYQQKPGQAPRLLIY<u>GAS</u>SRATGIPDRFSGSGSGTDFTLTITRLESEDFAVYYC<u>QQYGNSPLT</u>FGGGTKVEIK

CDR-L1:
(SEQ ID NO: 29)
QSLNSNY

CDR-L2:
(SEQ ID NO: 30)
GAS

CDR-L3:
(SEQ ID NO: 31)
QQYGNSPLT

In an embodiment of the invention, a further therapeutic agent is an antibody or antigen-binding fragment that binds to influenza Group II HA protein such as H1H14612N2; or an antibody or fragment that comprises $V_H$ and $V_L$ of H1H14612N2; or a heavy chain immunoglobulin comprising CDR-H1, CDR-H2 and CDR-H3 of H1H14612N2 (e.g., SEQ ID NOs: 41-43) and a light chain immunoglobulin comprising CDR-L1, CDR-L2 and CDR-L3 of H1H14612N2 (e.g., SEQ ID NOs: 45-47). "H1H14612N2" refers to any anti-group II HA antibody comprising such sequences.

H1H14612N2
Heavy chain variable region
(SEQ ID NO: 40)
EVQLVESGGGLVKPGGSLRLSCAAS<u>GFSFSGFS</u>MNWVRQAPGKGLEWVSS<u>ISTSGNYM</u>YYADSVKGRFTISRDNAKKSFSLQMNSLRAEDSAIYYC<u>ARGGGYNWNLFDY</u>WGQGSLVTVSS

CDR-H1:
(SEQ ID NO: 41)
GFSFSGFS

CDR-H2:
(SEQ ID NO: 42)
ISTSGNYM

CDR-H3:
(SEQ ID NO: 43)
ARGGGYNWNLFDY

-continued
Light chain variable region
(SEQ ID NO: 44)
EIVLTQSPGTLSLSPGERATLSCRAS<u>QSLNSNY</u>LAWYQQKPGQAPRLLIY<u>GAS</u>SRATGIPDRFSGSGSGADFTLTISRLESEDFAVYYC<u>QQYGNSPLT</u>FGGGTKVEIK

CDR-L1:
(SEQ ID NO: 45)
QSLNSNY

CDR-L2:
(SEQ ID NO: 46)
GAS

CDR-L3:
(SEQ ID NO: 47)
QQYGNSPLT

In an embodiment of the invention, a further therapeutic agent is an antibody or antigen-binding fragment that binds to influenza Group I HA protein such as H1H11729P; or an antibody or fragment that comprises $V_H$ and $V_L$ of H1H11729P; or a heavy chain immunoglobulin comprising CDR-H1, CDR-H2 and CDR-H3 of H1H11729P (e.g., SEQ ID NOs: 33-35) and a light chain immunoglobulin comprising CDR-L1, CDR-L2 and CDR-L3 of H1H11729P (e.g., SEQ ID NOs: 37-39). "H1H11729P" refers to any anti-group I HA antibody comprising such sequences.

H1H11729P
Heavy chain variable region
(SEQ ID NO: 32)
QVQLVQSGAEVKKSGSSVKVSCKAS<u>GGTFSSYA</u>ISWVRQAPGQGLEWMGG<u>IIPIFGTP</u>SYAQKFQDRVTITTDESTSTVYMELSSLRSEDTAVYYC<u>ARQQPVYQYNMDV</u>WGQGTTVTVSS

CDR-H1:
(SEQ ID NO: 33)
GGTFSSYA

CDR-H2:
(SEQ ID NO: 34)
IIPIFGTP

CDR-H3:
(SEQ ID NO: 35)
ARQQPVYQYNMDV

Light chain variable region
(SEQ ID NO: 36)
DIQMTQSPSSLSASVGDRVTITCRAS<u>QGIRNN</u>LGWYQQKPLKAPKRLIY<u>AAS</u>SLQSGVPSRFSGSGSGTEFTLTISSLQPEDFATYYC<u>LQYNNYPWT</u>FGQGTKVEIK

CDR-L1:
(SEQ ID NO: 37)
QGIRNN

CDR-L2:
(SEQ ID NO: 38)
AAS

CDR-L3:
(SEQ ID NO: 39)
LQYNNYPWT

In a certain embodiment of the invention, the further therapeutic agent is not amantadine, rimantadine, oseltamivir, zanamivir, aprotinin, leupeptin, a cationic steroid antimicrobial, an influenza vaccine (e.g., killed, live, attenuated whole virus or subunit vaccine), or an antibody against influenza virus (e.g., an anti-hemagglutinin antibody).

The term "in association with" indicates that the components, an anti-TMPRSS2 antigen-binding protein, e.g., antibody or antigen-binding fragment thereof of the present invention, along with another agent such as oseltamivir, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein an anti-TMPRSS2 antibody or antigen-binding fragment thereof.

Kits

Further provided are kits comprising one or more components that include, but are not limited to, an anti-TMPRSS2 antigen-binding protein, e.g., an antibody or antigen-binding fragment as discussed herein (e.g., H1H7017N or H4H7017N), in association with one or more additional components including, but not limited to, a further therapeutic agent, as discussed herein. The antigen-binding protein and/or the further therapeutic agent can be formulated as a single composition or separately in two or more compositions, e.g., with a pharmaceutically acceptable carrier, in a pharmaceutical composition.

In one embodiment of the invention, the kit includes an anti-TMPRSS2 antigen-binding protein, e.g., an antibody or antigen-binding fragment thereof of the invention (e.g., H1H7017N or H4H7017N), or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-TMPRSS2 antigen-binding protein, e.g., antibody or antigen-binding fragment thereof of the invention (e.g., H1H7017N or H4H7017N), or pharmaceutical composition thereof in combination with one or more further therapeutic agents formulated together, optionally, in a pharmaceutical composition, in a single, common container.

If the kit includes a pharmaceutical composition for parenteral administration to a subject, the kit can include a device (e.g., an injection device) for performing such administration. For example, the kit can include one or more hypodermic needles or other injection devices as discussed above containing the anti-TMPRSS2 antigen-binding protein, e.g., antibody or antigen-binding fragment thereof of the present invention (e.g., H1H7017N or H4H7017N).

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Diagnostic Uses of the Antibodies

The anti-TMPRSS2 antigen-binding proteins, e.g., antibodies or antigen-binding fragments thereof of the present invention (e.g., H1H7017N or H4H7017N), may be used to detect and/or measure TMPRSS2 in a sample. Exemplary assays for TMPRSS2 may include, e.g., contacting a sample with an anti-TMPRSS2 antigen-binding protein of the invention, wherein the anti-TMPRSS2 antigen-binding protein is labeled with a detectable label or reporter molecule or used as a capture ligand to selectively isolate TMPRSS2 from samples. The presence of an anti-TMPRSS2 antigen-binding protein complexed with TMPRSS2 indicates the presence of TMRPSS2 in the sample. Alternatively, an unlabeled anti-TMPRSS2 antibody can be used in combination with a secondary antibody which is itself detectably labeled. The detectable label or reporter molecule can be a radioisotope, such as 3H, 14C, 32P, 35S, or 125I; a fluorescent or chemiluminescent moiety such as fluorescein isothiocyanate, or rhodamine; or an enzyme such as alkaline phosphatase, 3-galactosidase, horseradish peroxidase, or luciferase. Specific exemplary assays that can be used to detect or measure TMPRSS2 in a sample include enzyme-linked immunosorbent assay (ELISA), radioimmunoassay (RIA), and fluorescence-activated cell sorting (FACS). Thus, the present invention includes a method for detecting the presence of TMPRSS2 polypeptide in a sample comprising contacting the sample with an anti-TMPRSS2 antigen-binding protein and detecting the presence of a TMPRSS/anti-TMPRSS2 antigen-binding protein wherein the presence of the complex indicates the presence of TMPRSS2.

The present invention includes cell-based ELISA methods using the anti-TMPRSS2 antigen-binding proteins, e.g., antibodies and antigen-binding fragments thereof of the present invention (e.g., H1H7017N), to detect the presence of TMPRSS2 on a cell. In an embodiment of the invention, the method includes the steps:

(i) contacting cells immobilized to a solid surface (e.g., a microplate) to be tested for the presence of TMPRSS2 with an anti-TMPRSS2 antigen-binding protein of the present invention;

(ii) optionally washing the mixture to remove unbound anti-TMPRSS2 antigen-binding protein;

(iii) contacting the anti-TMPRSS2 antigen-binding protein with a labeled secondary antibody or antigen-binding fragment thereof that binds to the anti-TMPRSS2 antigen-binding protein;

(iv) optionally washing the complex to remove unbound antigen-binding protein; and (v) detecting the presence of the label on the secondary antibody or fragment, wherein detection of the label indicates that the cells contain TMPRSS2. For example, the present invention includes such cell-based ELISA methods for identifying TMPRSS2$^+$ cells in a sample.

An anti-TMPRSS2 antigen-binding protein of the invention (e.g., H1H7017N or H4H7017N) may be used in a Western blot or immune-protein blot procedure for detecting the presence of TMPRSS2 or a fragment thereof in a sample. Such a procedure forms part of the present invention and includes the steps of e.g.:

(1) providing a membrane or other solid substrate comprising a sample to be tested for the presence of TMPRSS2, e.g., optionally including the step of transferring proteins from a sample to be tested for the presence of TMPRSS2 (e.g., from a PAGE or SDS-PAGE electrophoretic separation of the proteins in the sample) onto a membrane or other solid substrate using a method known in the art (e.g., semi-dry blotting or tank blotting); and contacting the membrane or other solid substrate to be tested for the presence of TMPRSS2 or a fragment thereof with an anti-TMPRSS2 antigen-binding protein of the invention.

Such a membrane may take the form, for example, of a nitrocellulose or vinyl-based (e.g., polyvinylidene fluoride (PVDF)) membrane to which the proteins to be tested for the presence of TMPRSS2 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-TMPRSS2 antigen-binding protein, the membrane is optionally blocked, e.g., with non-fat dry milk or the like so as to bind non-specific protein binding sites on the membrane.

(2) washing the membrane one or more times to remove unbound anti-TMPRSS2 antigen-binding protein and other unbound substances; and (3) detecting the bound anti-TMPRSS2 antigen-binding protein.

Detection of the bound antigen-binding protein indicates that the TMPRSS2 protein is present on the membrane or substrate and in the sample. Detection of the bound antigen-binding protein may be by binding the antigen-binding protein with a secondary antibody (an anti-immunoglobulin antibody) which is detectably labeled and, then, detecting the presence of the secondary antibody label.

The anti-TMPRSS2 antigen-binding proteins (e.g., antibodies and antigen-binding fragments (e.g., H1H7017N or H4H7017N)) disclosed herein may also be used for immunohistochemistry. Such a method forms part of the present invention and comprises, e.g., (1) contacting tissue to be tested for the presence of TMPRSS2 protein with an anti-TMPRSS2 antigen-binding protein of the invention; and (2) detecting the antigen-binding protein on or in the tissue.

If the antigen-binding protein itself is detectably labeled, it can be detected directly. Alternatively, the antigen-binding protein may be bound by a detectably labeled secondary antibody wherein the label is then detected.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: In Vitro Multicycle Replication

The ability of the influenza virus, A/Puerto Rico/08/1934 (H1N1)-GFP, to replicate in Calu3, A549, MDCK and HepG2 cells was assessed.

TABLE 1

Reagents used.

| Description | Vendor |
| --- | --- |
| Calu-3 cells | American Type Culture Collection (ATCC) |
| A549 cells | American Type Culture Collection (ATCC) |

TABLE 1-continued

Reagents used.

| Description | Vendor |
| --- | --- |
| MDCK (London) cells | IRR |
| HepG2 cells | American Type Culture Collection (ATCC) |
| A/Puerto Rico/08/1934 (H1N1)-GFP | N/A |
| DMEM | Gibco |
| F12 | Gibco |
| Pen/Strep | Gibco |
| Low IgG BSA | Sigma |
| PBS | Life Technologies |
| Fetal Bovine Serum | Life Technologies |

Experimental Procedure

Calu-3 cells (ATCC HTB55), A549 cells (ATCC CCL-185), MDCK cells (IRR FR-58) and HepG2 cells (ATCC HB-8065) were diluted to 40,000 cells/well in a 96-well plate in DMEM:F12 medium with 5% FBS. The next day, A/Puerto Rico/08/1934 (H1N1) carrying a GFP reporter gene in the NS segment (B. Manicassamy et al., Analysis of in vivo dynamics of influenza virus infection in mice using a GFP reporter virus. Proc Natl Acad Sci USA. 2010 Jun. 22; 107(25):11531-6) was prepared at an MOI (multiplicity of infection) of 0.1 and 0.01 in DMEM:F12 with low IgG BSA after three washes. The virus was incubated on the cells for 1 h at 37° C. after which the virus was removed and the wells washed three more times. The number of infected cells was quantified at 24, 48, 72 and 142 h post-infection on a CTL-ImmunoSpot® S6 Universal Analyzer (Cellular Technology Limited, Cleveland, Ohio).

Results Summary and Conclusions

Figure 1B:
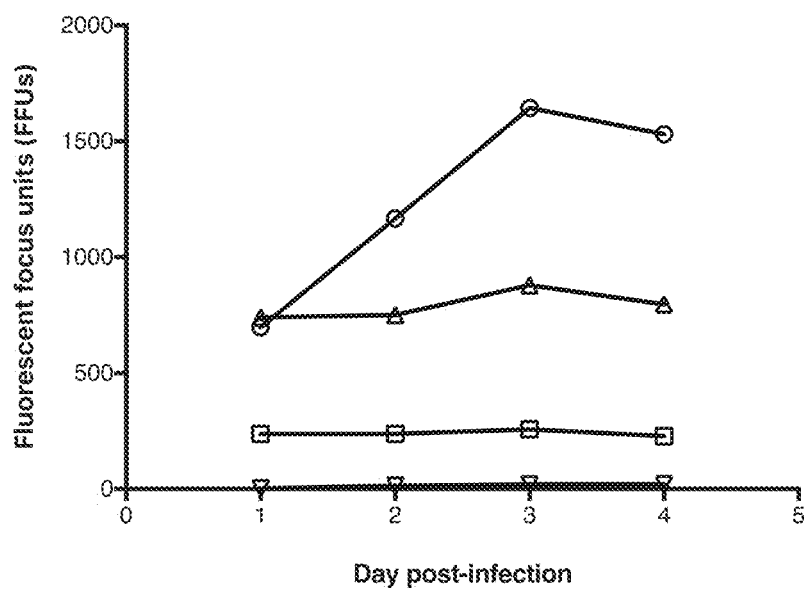
FIG. 1B shows the progression of the A/Puerto Rico/08/1934 (H1N1)-GFP virus spreading in different cell lines with an initial multiplicity of infection of 0.001 in absence of exogenous trypsin. Calu3 (circle), A549 (square), MDCK (triangle) and HepG2 (inverted triangle) cells.
Figure 2:
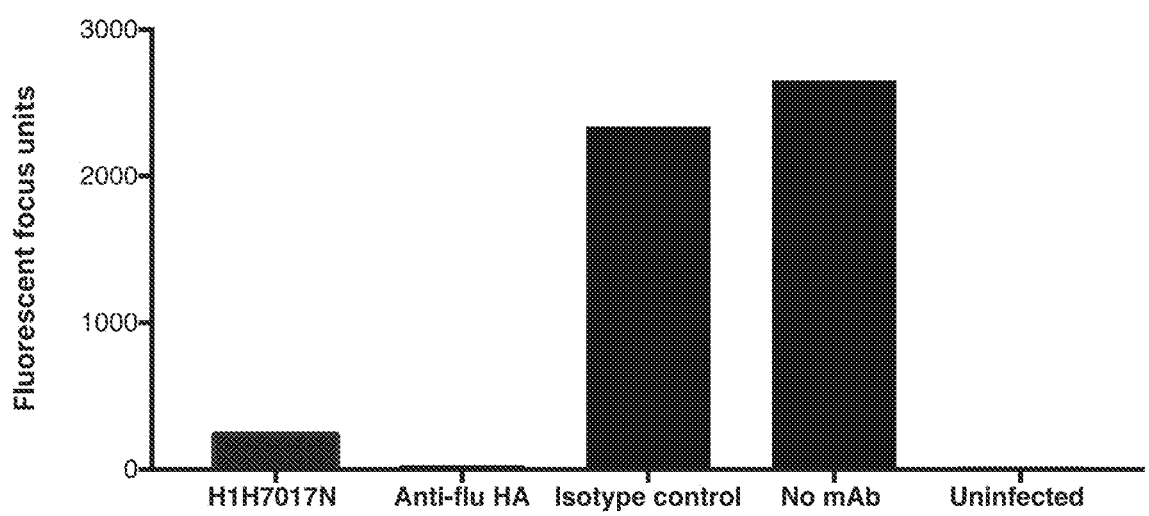
FIG. 2. shows application of H1H7017N during the infection cycle decreases the number of Fluorescent Focus Units (FFU) of A/Puerto Rico/08/1934 (H1N1) at 72 hours post-infection compared to isotype control antibody, no antibody, anti-HA antibody and uninfected controls.

Calu-3 is an immortalized human airway epithelial cell line which has been shown to allow multi-cycle replication of human influenza viruses in the absence of exogenous trypsin (Zeng et al., Highly pathogenic avian influenza H5N1 viruses elicit an attenuated type i interferon response in polarized human bronchial epithelial cells. Journal of Virology. 81, 12439-12449 (2007)). In addition, Calu-3 cells have been shown to express both TMPRSS2 and TMPRSS4, but not TMPRSS11D (HAT) at least at the mRNA level (Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011)). To confirm that Calu-3 cells can support the proteolytic activation of influenza virus possessing hemagglutinin with a monobasic cleavage site, the growth of an H1N1 GFP reporter virus in Calu-3 cells was analyzed and replication over time with A549 (human alveolar basal epithelial), MDCK (Madin Darby canine kidney) and HepG2 (human liver carcinoma) cells in the absence of trypsin was compared. The cells were infected at a low MOI and, at the indicated timepoint, viral titers were determined by counting fluorescent focus spots. Table 2 and FIG. 1 show low levels of infection in A549, MDCK and HepG2 cells, while Calu-3 cells show significantly increased titers at every timepoint. Although Calu-3 cells have been shown to express TMPRSS2 and TMPRSS4 at the mRNA level, knockdown of TMPRSS2 reduced influenza virus titers by 100- to 1,000-fold (Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011)). The low level of viral titers in A549, MDCK and HepG2 cells in the absence of trypsin are probably due to the addition of cleaved virus (harvested from embryonated chicken eggs or from MDCK culture with trypsin), but the presence of another HA-activating protease could be an explanation.

TABLE 2

Number of infected cells represented by Fluorescent Focus Units (FFU) on different days post-infection with a MOI of 0.1 or 0.01 in different cell types after infection with A/Puerto Rico/08/1934 (H1N1)-GFP.

| Cell line | Day(s) post-infection | MOI 0.1 FFU | MOI 0.01 FFU |
|---|---|---|---|
| Calu3 | 1 | 697 | 54 |
| | 2 | 1167 | 201 |
| | 3 | 1644 | 376 |
| | 4 | 1530 | 500 |
| A549 | 1 | 238 | 35 |
| | 2 | 238 | 46 |
| | 3 | 258 | 53 |
| | 4 | 228 | 52 |
| MDCK | 1 | 740 | 77 |
| | 2 | 750 | 60 |
| | 3 | 879 | 58 |
| | 4 | 796 | 53 |
| HepG2 | 1 | 3 | 1 |
| | 2 | 14 | 9 |
| | 3 | 20 | 13 |
| | 4 | 21 | 20 |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 27733646.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011).). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), May; 88(9):4744-51.doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 2006 October; 80(19):9896-8. PMID: 16973594.
10. B. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 2: Anti-TMPRSS2 Antibody H1H7017N Blocks Spread of Influenza in Vitro

The ability of various antibodies to reduce the titers of influenza virus A/Puerto Rico/08/1934 (H1N1) in Calu-3 cells was assessed.

TABLE 3

Reagents used.

| Description | Vendor |
|---|---|
| Calu-3 cells | ATCC |
| F12 | Gibco |
| FBS | Life Technologies |
| A/Puerto Rico/08/1934 (H1N1) | ATCC |
| DMEM | Gibco |
| Pen/Strep | Gibco |
| Low IgG BSA | Sigma |
| PBS | Life Technologies |
| Paraformaldehyde (16% w/v aq.) | Alfa Aesar |
| Triton X-100 | EMD |
| Anti-NP antibody | Millipore |
| Anti-Influenza A Antibody, nucleoprotein, clones A1, A3 Blend | |
| Goat anti-mouse IgG AF488 conjugated | Life Technologies |

Experimental Procedure

Calu-3 cells (ATCC HTB55) were diluted to 40,000 cells/well in a 96-well plate in DMEM:F12 medium with 5% FBS. The next day, the monoclonal antibodies were diluted to 166.7 nM in DMEM:F12 with low IgG BSA and added to the cells for 3 h at 37° C. and 5% $CO_2$. The mAb solution was removed and the cells were infected with A/Puerto Rico/08/1934 (H1N1) at an MOI of 0.001. The virus was incubated on the cells for 1 h at 37° C. in 5% $CO_2$ after which the virus was removed and the medium replaced with DMEM:F12 containing 166.7 nM mAbs. After 24 h and 48 h, the medium was replaced with fresh medium containing mAb and the cells were washed twice with PBS at 72 h. The cells were then fixed with 4% paraformaldehyde in PBS and virus detected using the anti-NP primary antibody at a 1:1000 dilution. The cells were incubated for 1 h and then washed and the secondary at 1:2000 dilution was added. The number of infected cells was quantified at on a CTL-ImmunoSpot® S6 Universal Analyzer (Cellular Technology Limited, Cleveland, Ohio).

Results Summary and Conclusions

Calu-3 is an immortalized human airway epithelial cell line which has been shown to allow multicycle replication of human influenza viruses in the absence of exogenous trypsin (Zeng et al., Highly pathogenic avian influenza H5N1 viruses elicit an attenuated type i interferon response in polarized human bronchial epithelial cells. Journal of Virology. 2007 November; 81(22):12439-49). In addition, Calu-3 cells have been shown to express both TMPRSS2 and TMPRSS4, but not TMPRSS11D (HAT) at least at the mRNA level (Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011)). It has been previously shown that Calu-3 cells supported the proteolytic activation of influenza virus—but inhibition of TMPRSS2 using the TMPRSS2-specific monoclonal antibody, H1H7017N was tested herein. The growth of A/Puerto Rico/08/1934 (H1N1) over 72 h after treating the cells with 166.7 nM of H1H7017N was analyzed. Viral titers were determined by counting fluorescent focus spots. Table 4 and FIG. 2 show decreased titers after treatment with antibody H1H7017N. Although Calu-3 cells have been shown to express TMPRSS2 and TMPRSS4 at the mRNA level, knockdown of TMPRSS2 reduced influenza virus titers by 100- to 1,000-fold (Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011)). The low level of existing viral titers in the absence of mAb were probably due to the addition of cleaved virus (harvested from embryonated chicken eggs or from MDCK culture with trypsin), but the presence of another HA-activating protease could also account for the presence of virus despite treatment with anti-TMPRSS2 mAb.

TABLE 4

Application of H1H7017N during the infection cycle decreases the number of Fluorescent Focus Units (FFU) of A/Puerto Rico/08/1934 (H1N1) at 72 hours post-infection.

| Treatment | Description | FFU |
|---|---|---|
| H1H7017N | Anti-TMPRSS2 mAb | 259 |
| H1H11729P | Anti-influenza A group 1 positive control | 18 |
| anti-hIgG4 with a mouse IgG2a Fc | IgG1 isotype control | 2338 |
| No mAb | Infection control | 2656 |
| Uninfected | Background control | 6 |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 27733646.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011).). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), May; 88(9):4744-51.doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 2006 October; 80(19):9896-8. PMID: 16973594.
10. B. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 3: FACS Analysis with MDCK/Tet-on, MDCK/Tet-on/hTMPRSS2, and MDCK/Tet-on/MfTMPRSS2 Cells The ability of anti-TMPRSS2 antibody, H1H7017N, to bind to MDCK cells expressing TMPRSS2 or not expressing TMPRSS2 was assessed.

TABLE 5

Reagents used.

| Reagent | Source |
|---|---|
| MDCK | ATCC |
| pLVX-EF1α-Tet3G | Clontech |
| pLVX Tight hTMPRSS2 Puro | |
| pLVX Tight MfTMPRSS2 Puro | |
| DMEM | Irvine Scientific |
| FBS | Seradigm |
| Pen/strep/glut | Invitrogen |
| Sodium Pyruvate 100 mM (100X) | Specialty Media |
| Geneticin ™ Selective Antibiotic (G418 Sulfate) | Invitrogen |
| Puromycin | Sigma |
| Doxycycline | Sigma |
| PBS without $Ca^{++}/Mg^{++}$ | Irvine Scientific |
| Accutase | Millipore |
| 96-well filter plates | Pall |
| BD CytoFix ™ | Becton Dickinson |
| Allophycocyanin (APC) AffiniPure $F(ab')_2$ Fragment Goat Anti-Human IgG, Fcγ Fragment Specific | Jackson Immuno |
| Control mAb1 (hIgG1 isotype control) | |
| Cytoflex | Beckman Coulter |
| FlowJo 10.1r5 | FlowJo |
| Prism 7 | Graphpad |

Experimental Procedure

Cell lines were developed to express human and cynomolgus monkey TMPRSS2 (hTMPRSS2 and mfTMPRSS2) in MDCK (Madin Darby Canine Kidney) cells upon induction with doxycycline. MDCK cells were transduced to stably express a modified tetracycline-controlled transactivator protein (Clontech) and the resulting cell line was termed MDCK/Tet-on cell line. MDCK/Tet-on cell line was transduced with a construct containing hTMPRSS2 (NP_005647.3 with a V160M) or mfTMPRSS2 (Ref seq XP_015302311.1 with S129L, N251S, I415V, R431Q, D492G) under the control of inducible promoter and the cell lines were termed MDCK/Tet-on/hTMPRSS2 and MDCK/Tet-on/mfTMPRSS2. The stable cell lines were maintained in growth media containing DMEM supplemented with 10% FBS, sodium pyruvate, penicillin/streptomycin/glutamine, 500 µg/mL G418 with or without 2 µg/mL puromycin.

For cell binding analysis by flow cytometry, cells were plated in growth media and incubated with doxycycline at 1 µg/mL for 16 hours to induce expression of TMPRSS2. Cells are detached using Accutase and resuspended in 1% FBS in PBS. Antibodies were serially diluted from 500 nM to 25 pM and each concentration of antibody was incubated with $1\times10^6$ cells at 4° C. for 30 minutes. A condition was included where no antibody was added to the cells. After incubation with primary antibodies, the cells were stained with allophycocyanin conjugated anti-human IgG secondary antibody at 1:1000 at 4° C. for 30 minutes. Cells were fixed using BD CytoFix™ and analyzed using CytoFLEX flow cytometer. Unstained and secondary antibody alone controls were also included for all cell lines. Geometric mean values of fluorescence for viable cells were determined using FlowJo software and the results were analyzed using non-linear regression (4-parameter logistics) with Prism 7 software (GraphPad) to obtain $EC_{50}$ values of cell binding by the antibodies.

Figure 3A:
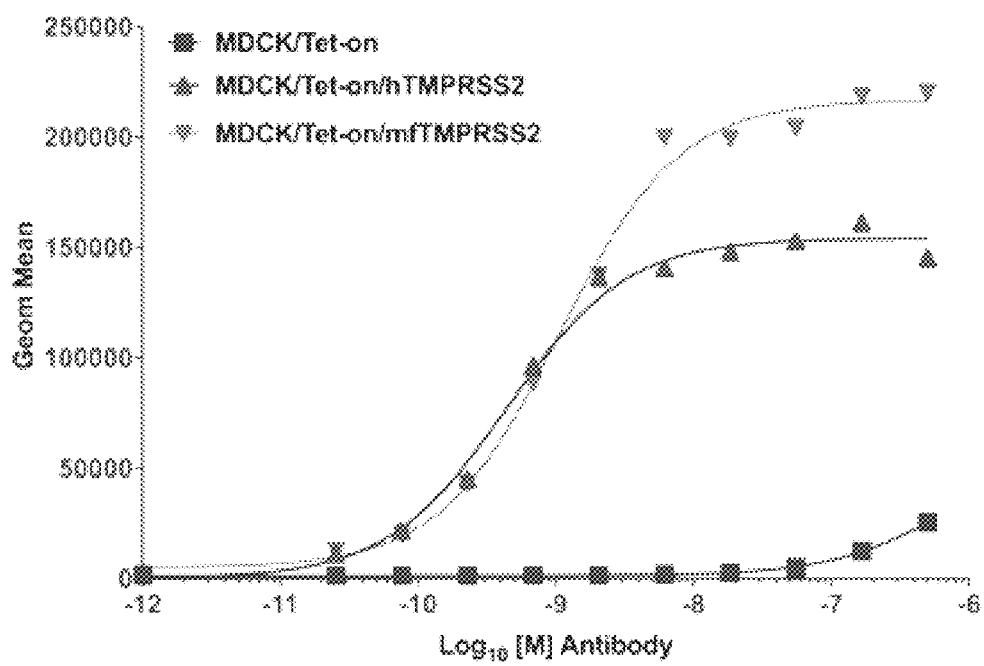
FIG. 3A shows anti-TMPRSS2, H1H7017N, binds to human and cynomolgus monkey TMPRSS2 expressed on cells. H1H7017N, bound to MDCK/Tet-on/hTMPRSS2 and MDCK/Tet-on/mfTMPRSS2 with EC50 values of 460 pM and 1.06 nM respectively and did not show significant binding to MDCK/Tet-on cells.
Figure 3B:
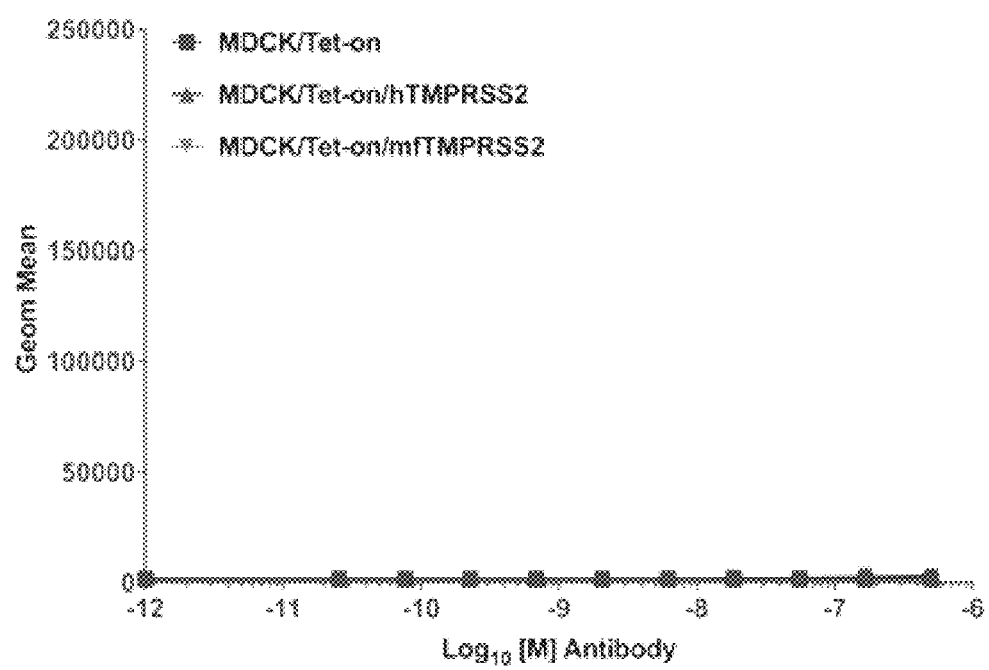
FIG. 3B shows anti-TMPRSS2, H1H7017N, binds to human and cynomolgus monkey TMPRSS2 expressed on cells. Control mAb1, an irrelevant isotype control antibody, did not show binding to any of the cell lines tested.

As shown in FIG. 3, the anti-hTMPRSS2 antibody of the invention, H1H7017N, bound to MDCK/Tet-on/hTMPRSS2 and MDCK/Tet-on/mfTMPRSS2 with $EC_{50}$ values of 460 pM and 1.06 nM respectively. H1H7017N did not show significant binding to MDCK/Tet-on cells. Control mAb1, an irrelevant isotype control antibody, did not show binding to any of the cell lines tested.

Example 4: Biacore Binding Kinetics of Anti-TMPRSS2 Monoclonal Antibodies Binding to Different TMPRSS2 Reagents Measured at 25° C. and 37° C.

Equilibrium dissociation constant ($K_D$) for different TMPRSS2 reagents binding to purified anti-TMPRSS2 monoclonal antibodies were determined using a real-time surface plasmon resonance based Biacore 4000 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with the rabbit anti-mouse Fc specific polyclonal antibody (GE Healthcare Cat #BR100838) to capture anti-TMPRSS2 monoclonal antibodies. Binding studies were performed on human TMPRSS2 extracellular domain expressed with a C-terminal myc-myc-hexahistidine tag (hTMPRSS2.mmh), and monkey TMPRSS2 extracellular domain expressed with a C-terminal myc-myc-hexahistidine tag (mfTMPRSS2.mmh). Different concentrations of HMM-hTMPRSS2 and HMM-mfTMPRSS2 (100 nM-6.25 nM; 4-fold serial dilution) were first prepared in HBS-ET running buffer and were injected over anti-mouse Fc captured anti-TMPRSS2 monoclonal antibody surface for 2.5 minutes at a flow rate of 30 µL/minute, while the dissociation of monoclonal antibody bound TMPRSS2 reagent was monitored for 7 minutes in HBS-ET running buffer. The association rate (ka) and dissociation rate (kd) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka},$$

$$\text{and } t1/2 \text{ (min)} = \frac{\ln(2)}{60 * kd}$$

Binding kinetics parameters for HMM-hTMPRSS2 or HMM-mfTMPRSS2 binding to different anti-TMPRSS2 monoclonal antibodies of the invention at 25° C. and 37° C. are shown in Tables 6 through 9.

At 25° C., anti-TMPRSS2 monoclonal antibodies bound to HMM-hTMPRSS2 with $K_D$ value 2.81 nM, as shown in Table 6. At 37° C., anti-HMM-hTMPRSS2 monoclonal antibodies bound to HMM-hTMPRSS2 with $K_D$ value 9.31 nM, as shown in Table 7.

At 25° C., anti-TMPRSS2 monoclonal antibodies bound to HMM-mfTMPRSS2 with $K_D$ value 56.0 nM, as shown in Table 8. At 37° C., anti-TMPRSS2 monoclonal antibodies bound to HMM-mfTMPRSS2 with $K_D$ value 140 nM, as shown in Table 9.

TMPRSS2 Proteins hTMPRSS2 knob_mmh (W106-R255).mmh:

amino acids 1-150: amino acids 106 through 255 of human TMPRSS2 (accession number NP_005647.3 with a V160M)

Amino acids: 151-178: myc-myc-hexahistidine tag

WKFMGSKCSNSGIECDSSGTCINPSNWCDGVSHCPGGEDENRCVRLYGPN

FILQMYSSQRKSWHPVCQDDWNENYGRAACRDMGYKNNFYSSQGIVDDSG

STSFMKLNTSAGNVDIYKKLYHSDACSSKAVVSLRCIACGVNLNSSRQSR

EQKLISEEDLGGEQKLISEEDLHHHHHH (SEQ ID NO: 20; myc tags underscored, His 6 tag doubly underscored)

mfTMPRSS2 knob_mmh (W106-R255).mmh:

Amino acids 1-150: amino acids 106-255 of monkey TMPRSS2 (accession number XP_005548700.1 with S129L, N251S)

Amino acids 151-178: myc-myc-hexahistidine tag

WKFMGSKCSDSGIECDSSGTCISLSNWCDGVSHCPNGEDENRCVRLYGPN

FILQVYSSQRKSWHPVCRDDWNENYARAACRDMGYKNSFYSSQGIVDNSG

ATSFMKLNTSAGNVDIYKKLYHSDACSSKAVVSLRCIACGVRSNLSRQSR

EQKLISEEDLGGEQKLISEEDLHHHHHH (SEQ ID NO: 21; myc tags underscored, His 6 tag doubly underscored)

Results

TABLE 6

Binding kinetics parameters of HMM-hTMPRSS2 binding to TMPRSS2 monoclonal antibodies at 25° C.

| mAb Captured | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM7017N | 510 ± 5.3 | 103 | 2.65E+05 | 7.45E−04 | 2.81E−09 | 15.5 |

* H2aM7017N is an antibody with the H1H7017N variable domains set forth herein and a mouse IgG2a Fc.

TABLE 7

Binding kinetics parameters of HMM-hTMPRSS2 binding to TMPRSS2 monoclonal antibodies at 37° C.

| mAb Captured | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM7017N | 587 ± 4.5 | 117 | 3.47E+05 | 3.23E−03 | 9.31E−09 | 3.6 |

TABLE 8

Binding kinetics parameters of HMM-mfTMPRSS2 binding to TMPRSS2 monoclonal antibodies at 25° C.

| mAb Captured | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM7017N | 484 ± 1.8 | 67 | 2.80E+05 | 1.57E−02 | 5.60E−08 | 0.7 |

TABLE 9

Binding kinetics parameters of HMM-mfTMPRSS2 binding to MSR1 monoclonal antibodies at 37° C.

| mAb Captured | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM7017N | 569 ± 1.6 | 48 | 3.66E+05 | 5.12E−02 | 1.40E−07 | 0.2 |

Example 5: In Vitro Influenza Spread of Influenza H1, H3, and FluB Strains

In this example, the ability of various types of influenza to spread across an in vitro culture of Calu-3 cells and the effect of anti-TMPRSS2 antibodies on this spread was determined.

TABLE 10

Reagents used and lot numbers.

| Cat# | Description | Vendor |
|---|---|---|
| HTB55 | Calu-3 cells | ATCC (American Type Culture Collection) |
| 11995-073 | DMEM | Gibco |
| 211703 | F12 | Gibco |
| 15140-122 | Pen/Strep | Gibco |
| A033650ML | Low IgG BSA | Sigma |
| 10010-023 | PBS | Life Technologies |
| 26140079 | Fetal Bovine Serum | Life Technologies |
| VR-1469 | Influenza A A/Puerto Rico/08/1934 (H1_PR34) | ATCC |
| NR-13658 | H1N1 A/CaliforniaA/04/2009 (H1_CA09) | BEI Resources |
| FR-28 | Influenza A/Brisbane/59/2007 (H1_Bris) | Influenza Reagent Resource |
| FR-1068 | Influenza A/Hong Kong/38982/2009 (H9N2) | Influenza Reagent Resource |
| 3483 | Influenza A H3N2 Kilbourne F108 A/Aichi/2/68 (HA, NA) × A/PR/8/34, Re-assorted X-31 | BEI Resources |
| NR-41795 | Influenza B/Florida/04/2006 (Florida) | ATCC |
| NR-12280 | Influenza B Malaysia (Malaysia) | ATCC |
| MAB8251 | Anti-Influenza A Antibody, nucleoprotein, clones A1, A3 Blend | Millipore |
| Ab20711 | Anti-Influenza B Virus Nucleoprotein antibody [B017] | Abcam |

TABLE 10-continued

Reagents used and lot numbers.

| Cat# | Description | Vendor |
|---|---|---|
| A-11001 | Goat anti-Mouse IgG (H + L) Cross-Absorbed Secondary Antibody, Alexa Fluor 488 | ThermoFisher Scientific |

Experimental Procedure

Calu-3 cells were seeded at 40,000 cells/well in a 96-well plate in DMEM:F12 medium with 5% FBS. The next day, influenza virus strains were diluted to a previously determined MOI (see Table 11) and antibodies were diluted to 100 µg/mL. In these experiments, the anti-HA and anti-TMPRSS2 antibodies had different mechanisms of action, therefore, the experimental procedure was different for these antibodies in order to appropriately test them. The anti-HA antibodies were pre-incubated with an individual influenza virus strain for one hour at 37° C. in a separate plate. After the preincubation period, the antibody/virus mixture was added to Calu-3 cells for one hour. The anti-TMPRSS2 antibody was preincubated with uninfected Calu-3 cells for three hours at 37° C. After the preincubation period, virus was added to the Calu-3 cells pre-incubated with anti-TMPRSS2 antibodies for one hour. After the hour-long infection, the cells were washed three times with PBS and fresh antibody was, added along with new medium, to each well. Additional antibody was added at 24 and 48 hours post-infection. At 72 hours post-infection, the cells were stained with an anti-NP and quantified on a CTL-ImmunoSpot® S6 Universal Analyzer (Cellular Technology Limited, Cleveland, Ohio).

TABLE 11A

Experiment 1.

| Influenza Strain | Final MOI |
|---|---|
| H1_PR34 | 0.001 |
| H1_CA09 | 0.001 |
| H1_Bris | 0.001 |
| H9N2 | 0.01 |
| H3N2 | 0.001 |

TABLE 11B

Experiment 2.

| Influenza Strain | Final MOI |
|---|---|
| H1_PR34 | 0.01 |
| Florida | 0.01 |
| Malaysia | 0.001 |

Results Summary and Conclusions

Calu-3 is an immortalized human airway epithelial cell line which has been shown to allow multicycle replication of human influenza viruses in the absence of exogenous trypsin (Zeng et al., Journal of Virology 81: 12439-12449 (2007)). In addition, Calu-3 cells have been shown to express TMPRSS2 (Böttcher-Friebertshäuser et al., Journal of Virology 85: 1554-1562 (2011)) which is essential for these experiments as an anti-TMPRSS2 antibody is being tested. In these experiments, whether or not H1H7017N, an anti-TMPRSS2 antibody, can prevent the spread in different strains of influenza was examined. In addition, the corresponding anti-HA antibody for the different strains as a positive control was run. As expected, there was an initial infection in the presence of the anti-TMPRSS2 antibody but H1H7017N successfully prevented the spread of infection of H1_PR34, H1_CA09, H1_Bris, H9N2, and H3N2. This can be observed by examining the differences in the number of infected cells between the anti-TMPRSS2-treated cells and the infected controls (Table 12). It was concluded that the anti-TMPRSS2 antibody was not able to prevent spread in either of the influenza B strains because the number of infected cells in the control and treated wells were the same. In comparison, the anti-HA antibodies were pre-incubated with the virus and prevented the initial infection. This can also be seen by comparing the number of infected cells. Counting of the infected cells was performed on the CTL machine and are reported in the tables below.

TABLE 12A

| Experiment 1. | | | | |
|---|---|---|---|---|
| Influenza Strain | Uninfected Control | Infected Control | Infected cells treated with group specific HA antibody | Infected cells treated with H1H7017N anti-TMPRSS2 antibody |
| H1_PR34 | 10 | 3847.5 | 3 | 1496 |
| H1_CA09 | 3.5 | 4645.4 | 1.5 | 17 |
| H1_Bris | 15.5 | 3882 | 0.5 | 1005 |
| H9N2 | 4.5 | 4172 | 4.5 | 196.5 |
| H3N2 | 7.5 | 3922 | 9 | 754.5 |

TABLE 12B

| Experiment 2. | | | | |
|---|---|---|---|---|
| Influenza Strain | Uninfected Control | Infected Control | Infected cells treated with group specific HA antibody | Infected cells treated with H1H7017N anti-TMPRSS2 antibody |
| H1_PR34 | 1 | 2848 | 18 | 60 |
| Florida | 4 | 1339 | 229 | 1234 |
| Malaysia | 10 | 1184 | 758 | 1451 |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.

6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25):11531-6. doi: 10.1073/pnas.0914994107. Epub 2010 Jun. 7. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 6: The Effect of Treatment with H1H7017N Alone in TMPRS22 Humanized Mice The ability of anti-TMPRSS2 antibodies to protect mice engineered to express the human TMPRSS2 protein from infection with H1N1 influenza virus was assessed.

TABLE 13

Reagents used and lot numbers.

| Cat# | Description | Vendor |
| --- | --- | --- |
| VR-1469 | Influenza A A/Puerto Rico/08/1934 (H1N1) | ATCC |
| 20012-043 | PBS Ketamine:Xylazine | Gibco |

TABLE 14 mAb Clone IDs.

| AbPID | Description |
| --- | --- |
| H1H7017N | anti-TMPRSS2 mAb |
| H1H1238N | IgG1 isotype control |

Experimental Procedure

These experiments were performed in 5-8 week-old male and female mice engineered to express the human TMPRSS2 protein. Mice were challenged with 150 plaque-forming units (PFUs) of H1N1. The mice were sedated with 2004 of Ketamine:Xylazine (12 mg/ml:0.5 mg/ml) via intraperitoneal injection and then infected with 204 of virus intranasally. Antibodies were delivered either subcutaneously (SC) one day before infection or intravenously (IV) on various days post infection (PI). The antibody dosing schedule varied between experiments (Table 15). Body weights were collected daily up to day 14 PI and mice were sacrificed when they lost 20% of their starting body weight. Results are reported as percent survival.

TABLE 15A

Antibody Dosing (Experiment 1).

| Antibody | Days PI | Dose | Delivery |
| --- | --- | --- | --- |
| H1H1238N | −1 | 5 mg/kg | SC |
| H1H7017N | −1, 0 | 5 mg/kg | SC, IV |

TABLE 15B

Antibody Dosing (Experiment 2).

| Antibody | Days PI | Dose | Delivery |
| --- | --- | --- | --- |
| H1H1238N | 0 | 10 mg/kg | IV |
| H1H7017N | 0, 1, 2, 3 | 10 mg/kg | IV |

Results Summary and Conclusions

Figure 4:
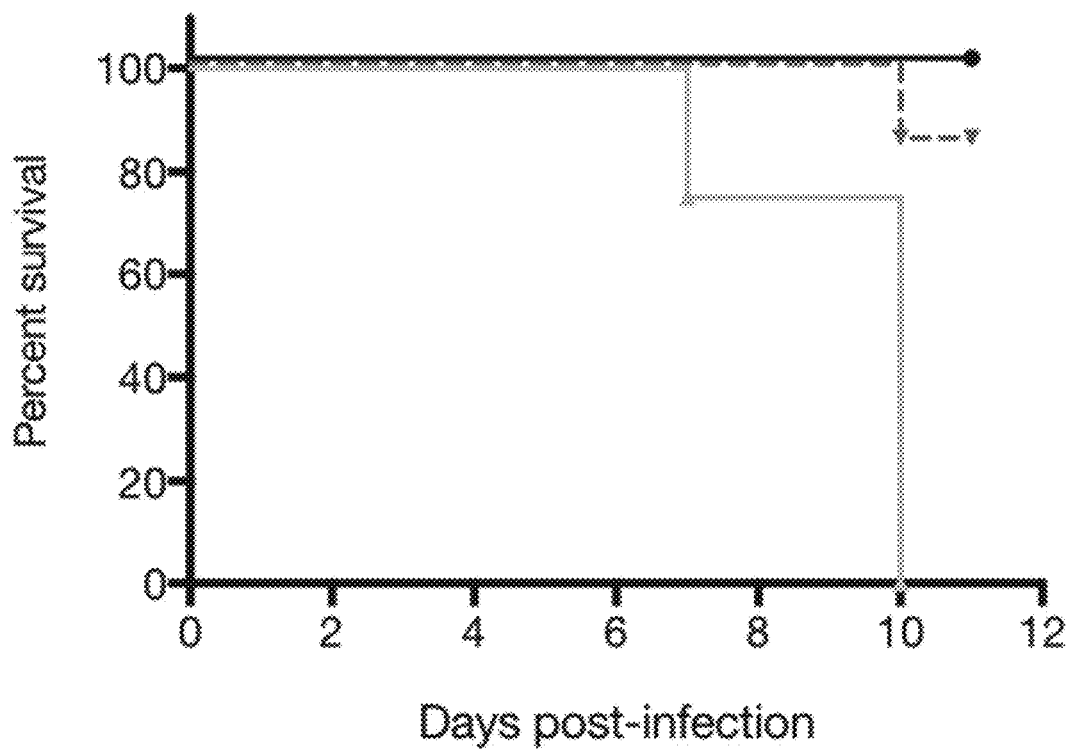
FIG. 4. shows a survival curve of a mouse engineered to express the human TMPRSS2 protein treated with 5 mg/kg of H1H7017N on day −1 PI (inverted triangle, dashed line) or day 0 PI (circle, solid line) showing protection against H1N1 in a prophylactic model. Mice treated with the isotype control H1H1238N (triangle, solid line) showed no protection.
Figure 5:
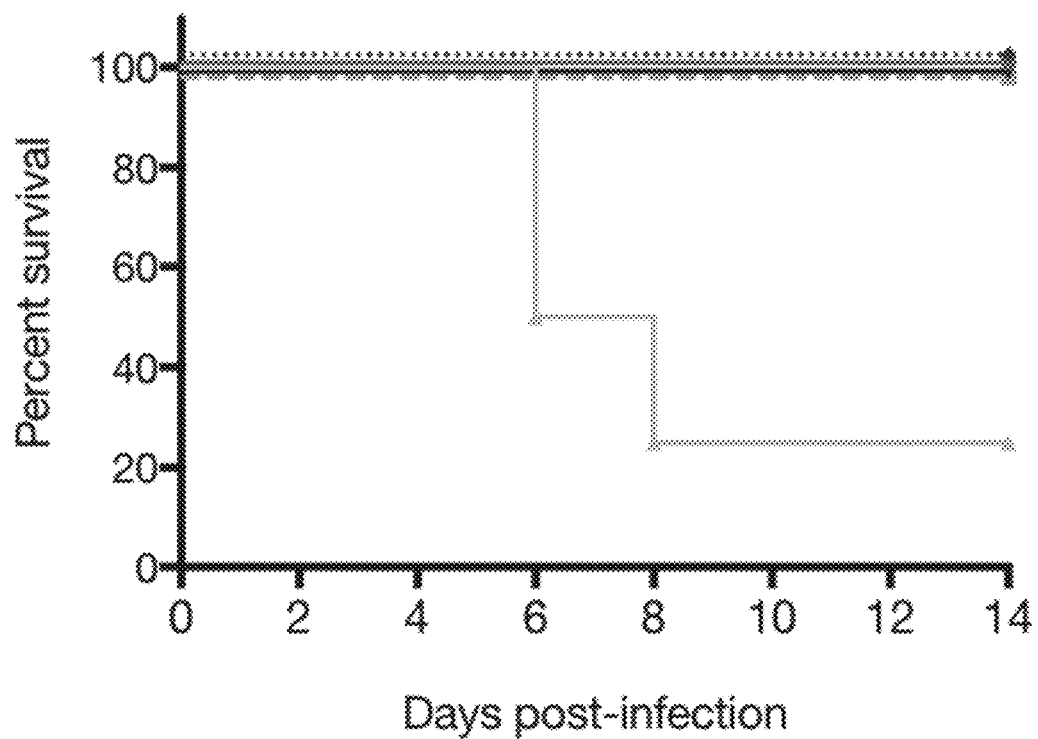
FIG. 5 shows a survival curve of a mouse engineered to express the human TMPRSS2 protein infected with H1N1, treated with 10 mg/kg H1H7017N demonstrating protection. Mice were treated on day 0 (diamond, dotted line), day 1 (circle, solid line), day 2 (inverted triangle, solid line), or day 3 PI (square, dashed line). The isotype control H1H1238N (triangle, solid line) had partial protection with a 25% survival rate.

It has been shown that mice engineered to express the human TMPRSS2 protein can be infected with a lethal dose of influenza. The aim of these experiments was to demonstrate that H1H7017N can protect mice engineered to express the human TMPRSS2 protein against influenza A group 1. The antibody was tested in prophylactic and therapeutic models. Treatment with H1H7017N resulted in higher survival than the isotype control (H1H1238N) treated mice in both experiments (FIGS. 4 and 5). In the prophylactic experiment, the survival was 0% for mice treated with H1H1238N, 85.7% for mice treated on day −1 PI, and 100% for mice treated on day 0 PI with H1H7017N. For the therapeutic model, the H1H1238N-treated group resulted in 25% survival while the groups treated with H1H7017N on day 0-3 PI resulted in 100% survival. Data are summarized in Table 16. H1H7017N shows efficacy in mice engineered to express the human TMPRSS2 protein.

TABLE 16A

Tabulated Data Summary (Experiment 1).

| Group ID | Number of mice per group | Percent survival (no. of surviving mice/total no. of mice in the group) |
| --- | --- | --- |
| H1H1238N, Day −1 PI, SC | 4 | 0 (0/4) |
| H1H7017N, Day −1 PI, SC | 7 | 85.7 (6/7) |
| H1H7017N, Day 0 PI, IV | 6 | 100 (6/6) |

TABLE 16B

Tabulated Data Summary (Experiment 2).

| Group ID | Number of mice per group | Percent survival (no. of surviving mice/total no. of mice in the group) |
| --- | --- | --- |
| H1H1238N, Day 0 PI, IV | 4 | 25 (1/4) |
| H1H7017N, Day 0 PI, IV | 5 | 100 (5/5) |
| H1H7017N, Day 1 PI, IV | 5 | 100 (5/5) |
| H1H7017N, Day 2 PI, IV | 5 | 100 (5/5) |
| H1H7017N, Day 3 PI, IV | 5 | 100 (5/5) |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. Epub 2010 Jun. 7. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 7: Anti-TMPRSS2 mAb, H1H7017N, Activity in TMPRSS2 Humanized Mouse Model The ability of anti-TMPRSS2 antibodies to protect a mouse engineered to express the human TMPRSS2 protein from infection with H3N2 influenza virus was assessed.

TABLE 17 mAb Clone IDs.

| AbPID | Description |
| --- | --- |
| H1H7017N | Anti-TMPRSS2 antibody |

TABLE 18

Reagents used and lot numbers.

| Cat# | Description | Vendor |
| --- | --- | --- |
| 3483 | Influenza A H3N2 Kilbourne F108 A/Aichi/2/68 (HA, NA) × A/PR/8/34, Reassorted X-31 | BEI Resources |
| 20012-043 | PBS Ketamine:Xylazine | Gibco |

Experimental Procedure

Eleven week-old male and female mice engineered to express the human TMPRSS2 protein were challenged with 20,000 plaque-forming units (PFUs) of H3N2. The mice were sedated with 2004 of Ketamine:Xylazine (12 mg/ml: 0.5 mg/ml) via intraperitoneal injection and then infected with 204 of virus intranasally. On day 1 or day 2 post-infection (PI), mice were intravenously injected with antibody. Mice were weighed and observed daily up to day 14 post-infection (PI). They were sacrificed when they lost 25% of their starting body weight.

Results Summary and Conclusions

Figure 6:
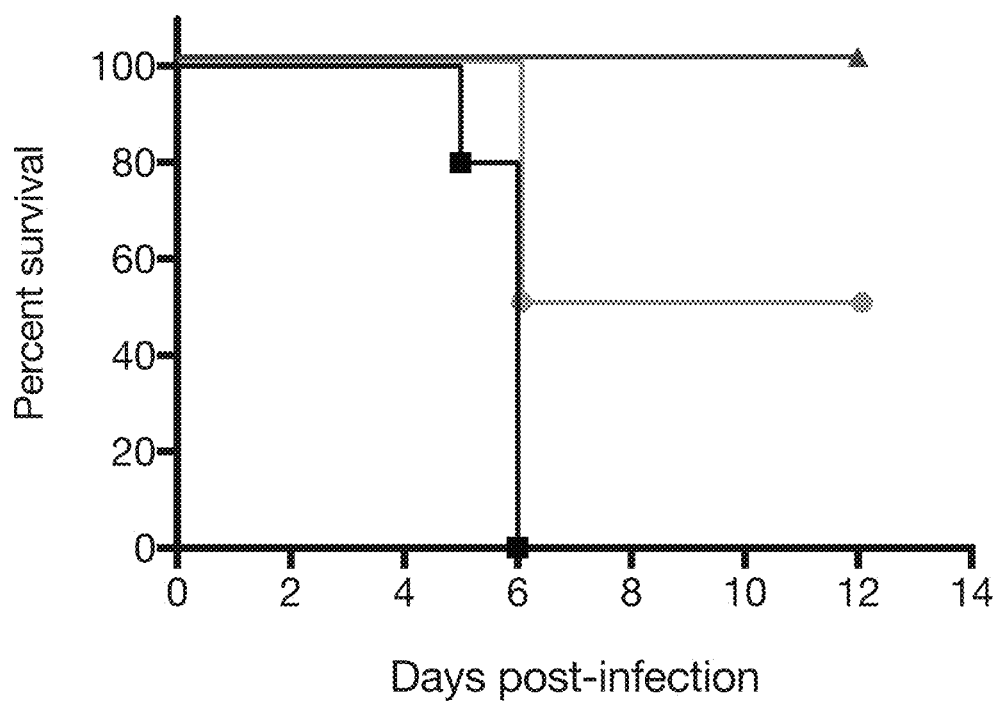
FIG. 6 shows a survival curve of hTPMRSS2 mice treated with 10 mg/kg of H1H7017N on day 1 PI (triangle) or day 2 PI (circle) showing protection against H3N2. Untreated mice (square) showed no protection.

Breadth is an important quality when considering an influenza therapy. It has already been demonstrated that anti-TMPRSS2 antibody H1H7017N was efficacious against influenza A group 1. The aim of this experiment was to demonstrate that H1H7017N can protect mice engineered to express the human TMPRSS2 protein against influenza A group 2. Mice engineered to express the human TMPRSS2 protein were infected with a lethal dose of H3N2 and treated on day 1 or day 2 PI. Both treatment groups had higher survival rates than the infected control. Mice treated on day 1 PI had a survival rate of 100% which was higher than the group treated on day 2 PI which had a 50% survival, while untreated mice had 0% survival. All mice died between days 5-6 PI. The survival graph is shown in FIG. 6 and % survival is summarized in Table 19. These results demonstrated that H1H7017 improved outcomes in an H3N2-lethal model.

TABLE 19

Tabulated Data Summary.

| Group ID | Number of mice per group | Percent survival (no. of surviving mice/total no. of mice in the group) |
| --- | --- | --- |
| Untreated | 5 | 0 (0/5) |
| H1H7017N, Day 1 PI | 5 | 100 (5/5) |
| H1H7017N, Day 0 PI, IV | 4 | 50 (2/4) |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. Epub 2010 Jun. 7. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 8: Infection of Mice Engineered to Express the Human TMPRSS2 Protein (Versus WT)

The survival of mice engineered to express the human TMPRSS2 protein infected with H1N1 influenza virus was assessed and compared with that of wild-type (WT) mice.

TABLE 20

| Reagents used and lot numbers. | | |
| --- | --- | --- |
| Cat# | Description | Vendor |
| VR-1469 | Influenza A A/Puerto Rico/08/1934 (H1N1) | ATCC |
| 20012-043 | PBS Ketamine:Xylazine | Gibco |

Experimental Procedure

Figure 7A:
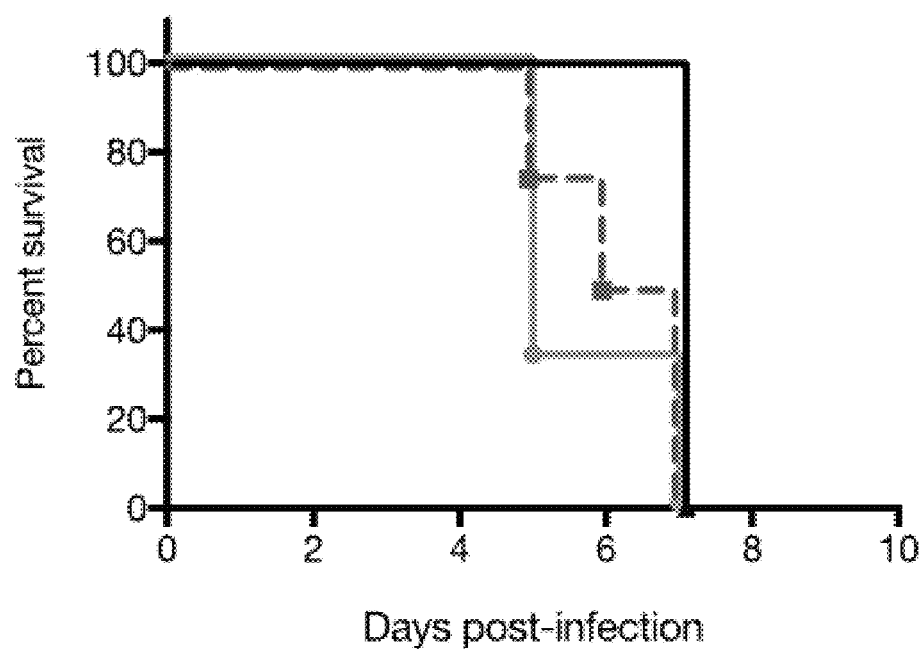
FIG. 7A shows a survival curve of wild-type mice infected with 150 PFUs (triangle), 750 PFUs (square), or 1,500 PFUs (circle) of A/Puerto Rico/08/1934 (H1N1). Mice were weighed daily until day 14 PI.
Figure 7B:
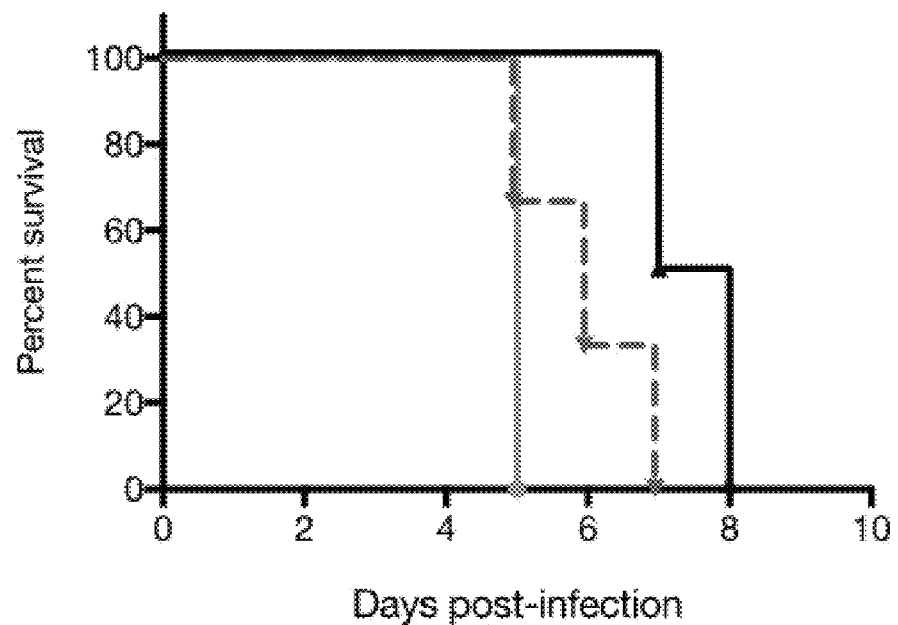
FIG. 7B shows a survival curve of mice engineered to express the human TMPRSS2 protein infected with 150 PFUs (triangle), 750 PFUs (square), or 1,500 PFUs (circle) of A/Puerto Rico/08/1934 (H1N1). Mice were weighed daily until day 14 PI.
Figure 8:
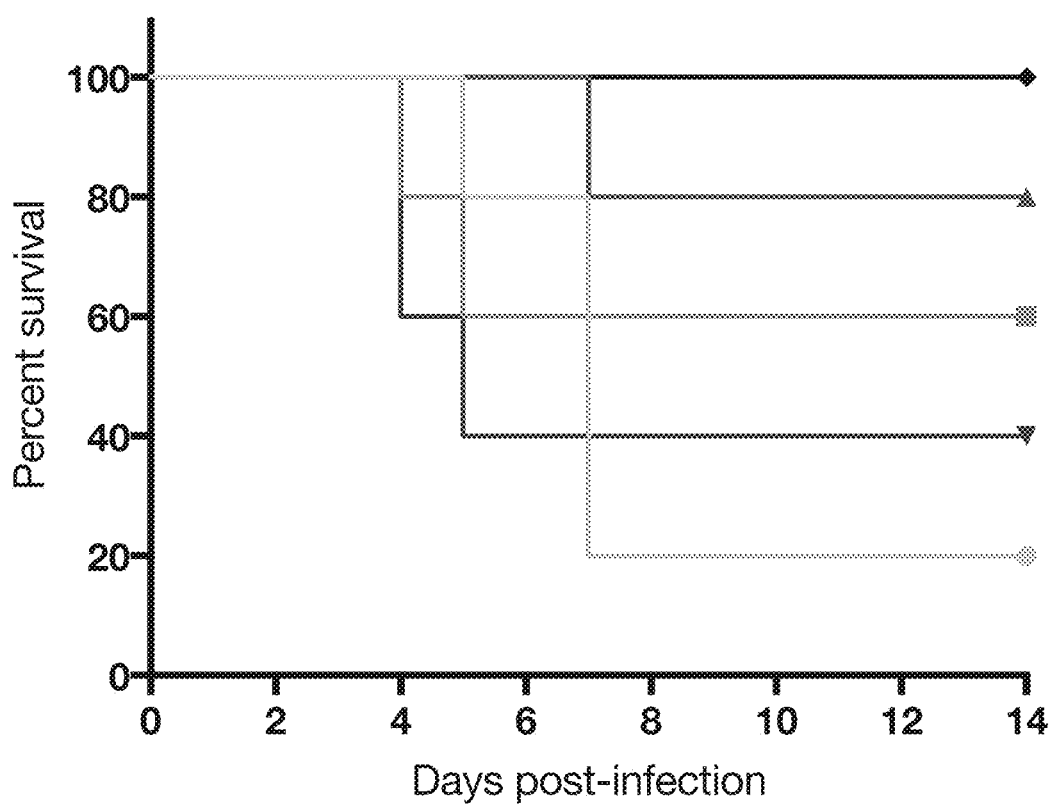
FIG. 8 shows a survival curve of a mouse engineered to express the human TMPRSS2 protein infected with A/Aichi/2/68 (HA, NA)×A/PR/8/34 (H3N2) on day 0 and treated with a combination of 2.5 mg/kg each of H1H7017N and H1H14611N2 (diamond), 10 mg/kg H1H7017N (triangle), 10 mg/kg H1H14611N2 (square), 5 mg/kg each of H1H7017N and H1H14611N2, or 10 mg/kg hIgG1 isotype control (circle). Mice were weighed daily until day 14 PI.

The experiment was performed in 7.5-8 week-old male and female mice engineered to express the human TMPRSS2 protein or wild-type littermates. Mice were challenged with 150, 750, or 1,500 plaque-forming units (PFUs) of A/Puerto Rico/08/1934 (H1N1). The mice were sedated with 2004 of Ketamine:Xylazine (12 mg/ml:0.5 mg/ml) via intraperitoneal injection and then infected with 204 of virus intranasally. Body weights were collected daily up to day 14 PI and mice were sacrificed when they lost 20% of their starting body weight. Results are reported as percent survival (FIG. 7).

Results Summary and Conclusions

Mice engineered to express the human TMPRSS2 protein were generated in order to test the therapeutic efficacy of the anti-TMPRSS2 antibodies in an influenza in vivo model. In this experiment, the survival rates of mice engineered to express the human TMPRSS2 protein and wild-type mice infected with 150, 750 or 1,500 PFUs of a historical strain of H1N1 was compared. There was 0% survival for mice engineered to express the human TMPRSS2 protein and wild-type mice in all three infection groups. All mice died between day 5 and day 8 PI, with those receiving a higher virus dose dying sooner than those who received a lower virus dose. The survival patterns of mice engineered to express the human TMPRSS2 protein were similar to the wild-type mice. This shows that mice engineered to express the human TMPRSS2 protein can be used as an influenza in vivo model to assess the effectiveness of TMPRSS2-specific antibodies. See Table 21.

TABLE 21

| Tabulated Data Summary. | | |
| --- | --- | --- |
| Group ID | Number of mice per group | Percent survival (no. of surviving mice/total no. of mice in the group) |
| Wild-type; 150 PFUs H1N1 | 4 | 0 (0/4) |
| Wild-type; 750 PFUs H1N1 | 4 | 0 (0/4) |
| Wild-type; 1,500 PFUs H1N1 | 3 | 0 (0/3) |
| Mice engineered to express the human TMPRSS2 protein; 150 PFUs H1N1 | 4 | 0 (0/4) |
| Mice engineered to express the human TMPRSS2 protein; 750 PFUs H1N1 | 3 | 0 (0/3) |
| Mice engineered to express the human TMPRSS2 protein; 1,500 PFUs H1N1 | 3 | 0 (0/3) |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. Epub 2010 Jun. 7. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 9: The Effect of Treatment with the Combination of H1H14611N2 and H1H7017N in Mice after Infection with H3N2

The ability of a combination of anti-TMPRSS2 and anti-influenza antibodies to protect mice engineered to express the human TMPRSS2 protein from infection with H3N2 influenza virus was assessed.

TABLE 22 mAb Clone IDs.

| AbPID | Description |
|---|---|
| H1H7017N | Anti-TMPRSS2 antibody |
| H1H14611N2 | Anti-influenza A group 2 antibody |
| H1H1238N | IgG1 isotype control |

TABLE 23

Reagents used and lot numbers.

| Description | Vendor |
|---|---|
| Influenza A H3N2 Kilbourne F108 A/Aichi/2/68 (HA, NA) × A/PR/8/34, Reassorted X-31 | BEI Resources |
| PBS | Gibco |
| Ketamine:Xylazine | |

Experimental Procedure

Eight week-old male and female mice engineered to express the human TMPRSS2 protein were challenged with 20,000 plaque-forming units (PFUs) of A/Aichi/2/68 (HA, NA)×A/PR/8/34, Re*assorted X-31 (H3N2). The mice were sedated with 200 μL of Ketamine:Xylazine (12 mg/ml:0.5 mg/ml) via intraperitoneal injection and then infected with 204 of virus intranasally. On day 4 post-infection (PI), mice were intravenously injected with antibody. Body weights were collected daily up to day 14 PI and mice were sacrificed when they lost 25% of their starting body weight. Results are reported as percent survival.

Results Summary and Conclusions

It has been shown that, individually, the TMPRSS2 antibody, H1H7017N, and the broad influenza A group 2 antibody, H1H14611N2, have therapeutic efficacy against a lethal mouse challenge with a historical strain of H3N2. It has also been shown that survival of mice infected with a lethal H1N1 challenge can be significantly increased after treatment with less total antibody than either alone through the combination of H1H7017N and the broad influenza A group 1 antibody, H1H11729P. The aim for this experiment was to evaluate the synergistic effect of H1H7017N and H1H14611N2 in combination. As shown in FIG. 8, 3 of 4 mice treated with the hIgG1 isotype control antibody at day 4 PI died by day 7 PI. 3 of 5 animals survived when dosed with 10 mg/kg of H1H14611N2 and 4 of 5 animals survived when dosed with 10 mg/kg of H1H7017N. When dosed in a combination of 5 mg/kg of each antibody, H1H14611N2 and H1H7017N, there was 40% survival. One hundred percent of mice treated with the combination of 2.5 mg/kg of each antibody, H1H14611N2 and H1H7017N, survived the challenge. Survival of mice infected with a lethal H3N2 challenge was increased through the combination of lower concentrations of H1H7017N and H1H14611N2 compared to higher concentrations of combined antibodies or either antibody alone. Percent survival is summarized in Table 24.

TABLE 24

Tabulated Data Summary.

| Group ID | Number of mice per group | Percent survival (no. of surviving mice/total no. of mice in the group) |
|---|---|---|
| 10 mg/kg hIgG1 isotype control | 5 | 20 (1/5) |
| 10 mg/kg H1H14611N2 | 5 | 60 (3/5) |
| 10 mg/kg H1H7017N | 5 | 80 (4/5) |
| 5 mg/kg H1H7017N + 5 mg/kg H1H14611N2 | 5 | 40 (2/5) |
| 2.5 mg/kg H1H7017N + 2.5 mg/kg H1H14611N2 | 5 | 100 (5/5) |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. Epub 2010 Jun. 7. PMID: 20534532.
11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

Example 10: The Effect of Treatment with the Combination of H1H11729P and H1H7017N in Mice after Infection with H1N1

The ability of a combination of anti-TMPRSS2 and anti-influenza antibodies to protect mice engineered to express the human TMPRSS2 protein from infection with H1N1 influenza virus was assessed.

TABLE 25 mAb Clone IDs.

| AbPID | Description |
|---|---|
| H1H7017N | Anti-TMPRSS2 antibody |
| H1H11729P | Anti-influenza A group 1 antibody |
| H1H1238N | IgG1 isotype control |

TABLE 26

Reagents used and lot numbers.

| Cat# | Description | Vendor |
|---|---|---|
| VR-1469 | Influenza A A/Puerto Rico/08/1934 (H1N1) | ATCC |
| 20012-043 | PBS Ketamine:Xylazine | Gibco |

Experimental Procedure

Five week-old male and female mice engineered to express the human TMPRSS2 protein were challenged with 1,500 plaque-forming units (PFUs) of H1N1. The virus was delivered by sedating the mice with 2004 of Ketamine:Xylazine (12 mg/ml:0.5 mg/ml) and delivering 204 of virus intranasally. On day 3 post-infection (PI), mice were intravenously injected with antibody. Body weights were collected daily up to day 14 PI and mice were sacrificed when they lost 25% of their starting body weight.

Results Summary and Conclusions

Figure 9:
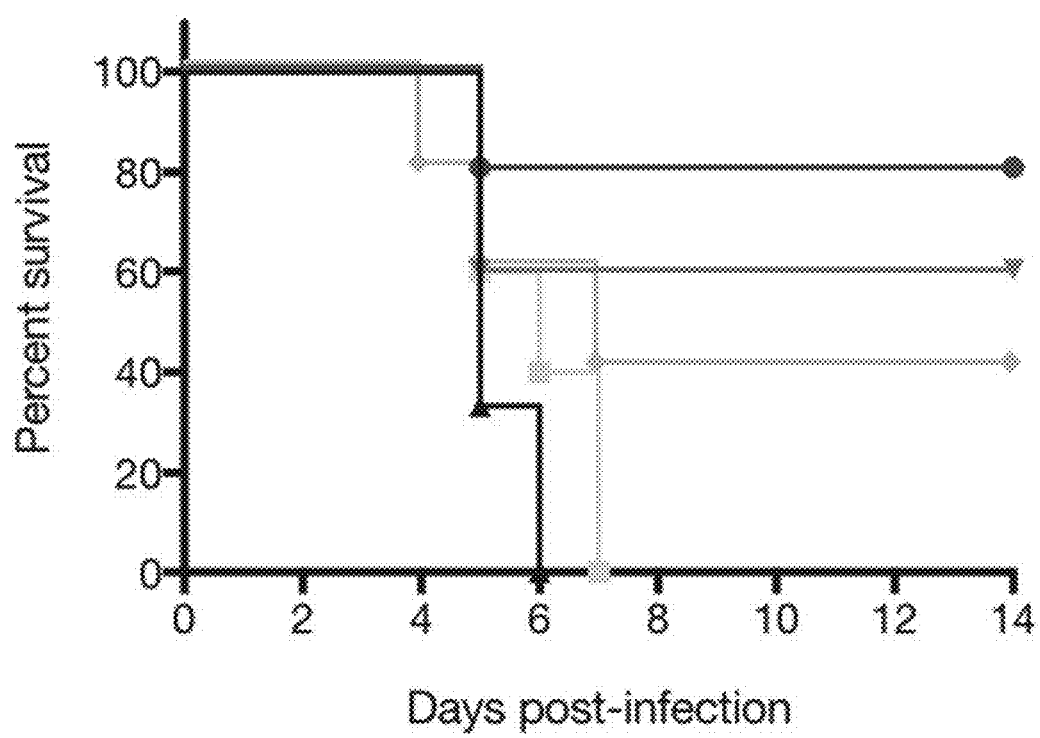
FIG. 9 shows a survival curve of a mouse engineered to express the human TMPRSS2 protein infected with A/Puerto Rico/08/1934 (H1N1) on day 1 PI and treated with a combination of 1 mg/kg of H1H7017N and 2 mg/kg of H1H11729P (circle), 2.5 mg/kg each of H1H7017N and H1H11729P (inverted triangle), 5 mg/kg H1H11729P (diamond), 5 mg/kg H1H7017N (square), or 5 mg/kg hIgG1 isotype control (triangle). Mice were weighed daily until day 14 PI.

It has been shown that, individually, the TMPRSS2 antibody, H1H7017N, and the broad influenza A group 1 antibody, H1H11729P, have therapeutic efficacy against a lethal mouse challenge with a historical strain of H1N1. However, the aim of this experiment was to evaluate the synergistic effect of the antibodies in combination. All mice treated with hIgG1 isotype control antibody at day 3 PI died by day 6 PI. When animals received 5 mg/kg of H1H11729P or H1H7017N, 40% and 0% of animals survived the infection, respectively. However, the combination of 2.5 mg/kg of each antibody, H1H11729P and H1H7017N, resulted in 60% survival. Eighty percent of mice treated with the combination of 1 mg/kg of H1H7017N and 2 mg/kg of H1H11729P (3 mg/kg total) survived the challenge. Survival of mice infected with a lethal H1N1 challenge was significantly increased after treatment with less total antibody than either alone through the combination H1H7017N and H1H11729P (See FIG. 9 and Table 27).

TABLE 27

Tabulated Data Summary.

| Group ID | Number of mice per group | Percent survival (no. of surviving mice/total no. of mice in the group) |
|---|---|---|
| 5 mg/kg hIgG1 isotype control | 3 | 0 (0/3) |
| 5 mg/kg H1H11729P | 5 | 40 (2/5) |
| 5 mg/kg H1H7017N | 5 | 0 (0/5) |
| 2.5 mg/kg H1H7017N + 2.5 mg/kg H1H11729P | 5 | 60 (3/5) |
| 1 mg/kg H1H7017N + 2 mg/kg H1H11729P | 5 | 80 (4/5) |

REFERENCES

1. K. Shirato, K. Kanou, M. Kawase, S. Matsuyama, Clinical Isolates of Human Coronavirus 229E Bypass the Endosome for Cell Entry. Journal of Virology. 91, e01387-16 (2017). PMID: 27733646.
2. L. M. Reinke et al., Different residues in the SARS-CoV spike protein determine cleavage and activation by the host cell protease TMPRSS2. PLoS ONE. 12, e0179177 (2017). PMID: 28636671.
3. Y. Zhou et al., Protease inhibitors targeting coronavirus and filovirus entry. Antiviral Research. 116, 76-84 (2015). PMID: 25666761.
4. P. Zmora, A.-S. Moldenhauer, H. Hofmann-Winkler, S. Pöhlmann, TMPRSS2 Isoform 1 Activates Respiratory Viruses and Is Expressed in Viral Target Cells. PLoS ONE. 10, e0138380 (2015). PMID: 26379044.
5. P. Zmora et al., Non-human primate orthologues of TMPRSS2 cleave and activate the influenza virus hemagglutinin. PLoS ONE. 12, e0176597 (2017). PMID: 28493964.
6. E. Böttcher-Friebertshäuser, D. A. Stein, H.-D. Klenk, W. Garten, Inhibition of influenza virus infection in human airway cell cultures by an antisense peptide-conjugated morpholino oligomer targeting the hemagglutinin-activating protease TMPRSS2. Journal of Virology. 85, 1554-1562 (2011). PMID: 21123387.
7. S. Bertram et al., TMPRSS2 and TMPRSS4 facilitate trypsin-independent spread of influenza virus in Caco-2 cells. Journal of Virology. 84, 10016-10025 (2010). PMID: 20631123.
8. C. Tarnow et al., TMPRSS2 is a host factor that is essential for pneumotropism and pathogenicity of H7N9 influenza A virus in mice. Journal of Virology (2014), doi:10.1128/JVI.03799-13. PMID: 24522916.
9. E. Bottcher et al., Proteolytic Activation of Influenza Viruses by Serine Proteases TMPRSS2 and HAT from Human Airway Epithelium. Journal of Virology. 80, 9896-9898 (2006). PMID: 16973594.
10. Manicassamy et al., Analysis of in vivo dynamics of influenza virus infection in mice using a GFP reporter virus. Proc Natl Acad Sci USA. 2010 Jun. 22; 107(25): 11531-6. doi: 10.1073/pnas.0914994107. Epub 2010 Jun. 7. PMID: 20534532.

11. H. Zeng et al., Highly pathogenic avian influenza H5N1 viruses elicit an attenuated type i interferon response in polarized human bronchial epithelial cells. Journal of Virology. 81, 12439-12449 (2007). PMID: 17855549.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants to relate to each and every individual publication, database entry (e.g., Genbank sequences or GeneID entries), patent application, or patent identified even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

I claim:

1. A method for treating or preventing cancer or infection with an influenza virus, coronavirus, SARS-Co virus, MERS-Co virus, parainfluenza virus, human metapneumovirus or hepatitis C virus (HCV), in a subject in need thereof, comprising administering a therapeutically effective amount of an antigen-binding protein that specifically binds to human TMPRSS2 comprising:
   (a) an immunoglobulin heavy chain variable region comprising the CDR-H1, CDR-H2, and CDR-H3 of an immunoglobulin heavy chain that comprises the amino acid sequence set forth in SEQ ID NO: 2, 17 or 19; and/or
   (b) an immunoglobulin light chain variable region comprising the CDR-L1, CDR-L2, and CDR-L3 of an immunoglobulin light chain that comprises the amino acid sequence set forth in SEQ ID NO: 4 or 18.

2. The method of claim 1 for treating or preventing cancer which is prostate cancer, colon cancer, lung cancer, pancreas cancer, urinary tract cancer, breast cancer, ovarian cancer, prostate adenocarcinoma, renal cell carcinoma, colorectal adenocarcinoma, lung adenocarcinoma, lung squamous cell carcinoma and/or pleural mesothelioma.

3. The method of claim 1, wherein the subject is administered one or more further therapeutic agents.

4. The method of claim 3 wherein the subject is administered one or more further therapeutic agents which is an anti-viral drug or a vaccine.

5. The method of claim 1, wherein the subject is administered one or more further therapeutic agents which is a member selected from the group consisting of:
   ledipasvir, sofosbuvir, a combination of ledipasvir and sofosbuvir, oseltamivir, zanamivir, ribavirin and interferon-alpha2b, interferon-alpha2a and an antibody or antigen-binding fragment thereof that specifically binds to influenza HA; and/or
   an antibody or antigen binding fragment thereof selected from the group consisting of H1H14611N2;

H1H14612N2; H1H11723P; H1H11820N; H1H11829N; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H2H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B.

6. A method for administering an antigen-binding protein that specifically binds to human TMPRSS2 into the body of a subject, wherein the antigen-binding protein comprises:
(a) an immunoglobulin heavy chain variable region comprising the CDR-H1, CDR-H2, and CDR-H3 of an immunoglobulin heavy chain that comprises the amino acid sequence set forth in SEQ ID NO: 2, 17 or 19; and/or
(b) an immunoglobulin light chain variable region comprising the CDR-L1, CDR-L2, and CDR-L3 of an immunoglobulin light chain that comprises the amino acid sequence set forth in SEQ ID NO: 4 or 18;
the method comprising injecting the antigen-binding protein into the body of the subject.

7. The method of claim 6 wherein the antigen-binding protein is injected into the body of the subject subcutaneously, intravenously or intramuscularly.

8. The method of claim 1, wherein the antigen-binding protein is an antibody or antigen-binding fragment thereof.

9. The method of claim 1, wherein the antigen-binding protein which is multispecific.

10. The method of claim 1, wherein the antigen-binding protein comprises:
a light chain immunoglobulin variable region that comprises:
(a) a CDR-L1 comprising the amino acid sequence: Q S I S S W (SEQ ID NO: 12),
(b) a CDR-L2 comprising the amino acid sequence: K A S (SEQ ID NO: 14),
(c) a CDR-L3 comprising the amino acid sequence: Q Q Y N S Y S Y T (SEQ ID NO: 16); and/or
a heavy chain immunoglobulin variable region that comprises:
(a) a CDR-H1 comprising the amino acid sequence: G F T F S S Y G (SEQ ID NO: 6),
(b) a CDR-H2 comprising the amino acid sequence: I W N D G S Y V (SEQ ID NO: 8),
(c) a CDR-H3 comprising the amino acid sequence: A R E G E W V L Y Y F D Y (SEQ ID NO: 10).

11. The method of claim 1, wherein the antigen-binding protein comprises:
(a) a heavy chain immunoglobulin that comprises the amino acid sequence set forth in SEQ ID NO: 17 or 19, or an immunoglobulin heavy chain variable region that comprises the amino acid sequence set forth in SEQ ID NO: 2;
and/or
(b) a light chain immunoglobulin that comprises the amino acid sequence set forth in SEQ ID NO: 18, or an immunoglobulin light chain variable region that comprises the amino acid sequence set forth in SEQ ID NO: 4.

12. The method of claim 1, wherein the antigen-binding protein comprises:
(a) an immunoglobulin heavy chain variable region comprising the amino acid sequence set forth in SEQ ID NO: 2; and
(b) an immunoglobulin light chain variable region comprising the amino acid sequence set forth in SEQ ID NO: 4 or 18.

13. The method of claim 1, wherein the antigen-binding protein comprises:
(a) the immunoglobulin heavy chain variable region comprising the amino acid sequence set forth in SEQ ID NO: 2; and
(b) the immunoglobulin light chain variable region comprising the amino acid sequence set forth in SEQ ID NO: 4.

14. The method of claim 1, wherein the antigen-binding protein comprises one or more of the following properties:
Inhibits growth of influenza virus in TMPRSS2-expressing cells;
Binds to the surface of TMPRSS-expressing cells;
Does not significantly bind to MDCK/Tet-on cells which do not express TMPRSS2;
Binds to human TMPRSS2 with a $K_D$ of about $2.81 \times 10^{-9}$ M at about 25° C.;
Binds to human TMPRSS2 with a $K_D$ of about $9.31 \times 10^{-9}$ M at about 37° C.;
Binds to cynomolgus TMPRSS2 with a $K_D$ of about $5.60 \times 10^{-8}$ M at about 25° C.;
Binds to cynomolgus TMPRSS2 with a $K_D$ of about $1.40 \times 10^{-7}$ M at about 37° C.;
Limits spread of influenza virus infection of cells in vitro; and/or
Protects mice engineered to express the human TMPRSS2 protein from death caused by influenza virus infection.

15. The method of claim 6, wherein the antigen-binding protein is an antibody or antigen-binding fragment thereof.

16. The method of claim 6, wherein the antigen-binding protein which is multispecific.

17. The method of claim 6, wherein the antigen-binding protein comprises:
a light chain immunoglobulin variable region that comprises:
(a) a CDR-L1 comprising the amino acid sequence: Q S I S W (SEQ ID NO: 12),
(b) a CDR-L2 comprising the amino acid sequence: K A S (SEQ ID NO: 14),
(c) a CDR-L3 comprising the amino acid sequence: Q Y N S Y S Y T (SEQ ID NO: 16); and/or
a heavy chain immunoglobulin variable region that comprises:
(a) a CDR-H1 comprising the amino acid sequence: G F T F S Y G (SEQ ID NO: 6),
(b) a CDR-H2 comprising the amino acid sequence: I W N D G S Y V (SEQ ID NO: 8),
(c) a CDR-H3 comprising the amino acid sequence: A R E G E W V L Y F D Y (SEQ ID NO: 10).

18. The method of claim 6, wherein the antigen-binding protein comprises:
(a) a heavy chain immunoglobulin that comprises the amino acid sequence set forth in SEQ ID NO: 17 or 19, or an immunoglobulin heavy chain variable region that comprises the amino acid sequence set forth in SEQ ID NO: 2;
and/or
(b) a light chain immunoglobulin that comprises the amino acid sequence set forth in SEQ ID NO: 18, or an immunoglobulin light chain variable region that comprises the amino acid sequence set forth in SEQ ID NO: 4.

19. The method of claim 6, wherein the antigen-binding protein comprises:
(a) an immunoglobulin heavy chain variable region comprising the amino acid sequence set forth in SEQ ID NO: 2; and
(b) an immunoglobulin light chain variable region comprising the amino acid sequence set forth in SEQ ID NO: 4 or 18.

20. The method of claim 6, wherein the antigen-binding protein comprises:

(a) the immunoglobulin heavy chain variable region comprising the amino acid sequence set forth in SEQ ID NO: 2; and
(b) the immunoglobulin light chain variable region comprising the amino acid sequence set forth in SEQ ID NO: 4.

* * * * *